(12) United States Patent
Cannon et al.

(10) Patent No.: US 7,906,323 B2
(45) Date of Patent: Mar. 15, 2011

(54) AUTOMATED BIOCULTURE AND BIOCULTURE EXPERIMENTS SYSTEM

(75) Inventors: Thomas F. Cannon, Glenwood, MD (US); Laura K. Cohn, Alexandria, VA (US); Peter D. Quinn, Washington, DC (US); Paul Kosnik, Gaithersburg, MD (US)

(73) Assignee: Tissue Genesis, Inc., Honolulu, HI (US)

( * ) Notice: Subject to any disclaimer, the term of this patent is extended or adjusted under 35 U.S.C. 154(b) by 1190 days.

(21) Appl. No.: 11/063,599

(22) Filed: Feb. 24, 2005

(65) Prior Publication Data
US 2005/0186671 A1    Aug. 25, 2005

Related U.S. Application Data

(60) Division of application No. 10/109,712, filed on Apr. 1, 2002, now abandoned, which is a continuation-in-part of application No. 09/967,995, filed on Oct. 2, 2001, now Pat. No. 7,270,996.

(51) Int. Cl.
*C12M 3/00* (2006.01)
*C12M 1/34* (2006.01)

(52) U.S. Cl. ............... 435/293.1; 435/297.2; 435/303.1; 435/809; 435/287.1

(58) Field of Classification Search ............... 435/293.1, 435/286.5, 303.1, 309.1, 309.2, 809, 287.1, 435/297.2
See application file for complete search history.

(56) References Cited

U.S. PATENT DOCUMENTS

| | | | |
|---|---|---|---|
| 3,753,865 A * | 8/1973 | Belzer et al. | 435/284.1 |
| 4,087,327 A | 5/1978 | Feder et al. | |
| 4,228,242 A | 10/1980 | Girard et al. | |
| 4,242,459 A | 12/1980 | Chick et al. | |
| 4,246,120 A | 1/1981 | Baudet et al. | |
| 4,310,630 A | 1/1982 | Girard et al. | |
| 4,311,798 A | 1/1982 | Katinger et al. | |

(Continued)

FOREIGN PATENT DOCUMENTS

WO    WO 97/16527    5/1997

(Continued)

OTHER PUBLICATIONS

"A Blood Vessel Model Constructed from Collagen and Cultured Vascular Cells", by Crispin B. Weinberg and Eugene Bell, Science, vol. 231, Jan. 1986, pp. 397-400.

(Continued)

*Primary Examiner* — William H Beisner
(74) *Attorney, Agent, or Firm* — Nixon Peabody LLP

(57) ABSTRACT

The present invention provides a feedback controlled bioculture platform for use as a precision cell biology research tool and for clinical cell growth and maintenance applications. The system provides individual closed-loop flowpath cartridges, with integrated, aseptic sampling and routing to collection vials or analysis systems. The system can operate in a standard laboratory or other incubator for provision of requisite gas and thermal environment. System cartridges are modular and can be operated independently or under a unified system controlling architecture, and provide for scale-up production of cell and cell products for research and clinical applications. Multiple replicates of the flowpath cartridges allow for individual, yet replicate cell culture growth and multiples of the experiment models that can be varied according to the experiment design, or modulated to desired cell development of cell culture end-points. The integral flowpath cartridge aseptic sampling system provides for dynamic analysis of metabolic products or representative cells from the culture.

5 Claims, 20 Drawing Sheets

U.S. PATENT DOCUMENTS

| | | | |
|---|---|---|---|
| 4,391,912 A | 7/1983 | Yoshida et al. | |
| 4,440,853 A | 4/1984 | Michaels et al. | |
| 4,442,206 A | 4/1984 | Michaels et al. | |
| 4,537,860 A | 8/1985 | Tolbert et al. | |
| 4,546,083 A | 10/1985 | Meyers et al. | |
| 4,647,539 A | 3/1987 | Bach | |
| 4,649,114 A | 3/1987 | Miltenburger et al. | |
| 4,722,902 A | 2/1988 | Harm et al. | |
| 4,748,124 A | 5/1988 | Vogler | |
| 4,808,315 A | 2/1989 | Manabe et al. | |
| 4,889,812 A | 12/1989 | Guinn et al. | |
| 4,942,770 A | 7/1990 | Seifert et al. | |
| 4,999,298 A | 3/1991 | Wolfe et al. | |
| 4,999,307 A | 3/1991 | Oakley | |
| 5,081,035 A | 1/1992 | Halberstadt et al. | |
| 5,202,254 A | 4/1993 | Amiot et al. | |
| 5,338,662 A | 8/1994 | Sadri | |
| 5,368,555 A | 11/1994 | Sussman et al. | |
| 5,416,022 A | 5/1995 | Amiot | |
| 5,424,209 A | 6/1995 | Kearney | |
| 5,494,822 A | 2/1996 | Sadri | |
| 5,612,188 A | 3/1997 | Shuler et al. | |
| 5,656,421 A | 8/1997 | Gebhard et al. | |
| 5,688,687 A | 11/1997 | Palsson et al. | |
| 5,792,603 A | 8/1998 | Dunkelman et al. | |
| 5,827,238 A * | 10/1998 | Kelley | 604/250 |
| 5,863,531 A | 1/1999 | Naughton et al. | |
| 5,985,653 A | 11/1999 | Armstrong et al. | |
| 5,989,913 A | 11/1999 | Anderson et al. | |
| 5,994,129 A | 11/1999 | Armstrong et al. | |
| 6,008,010 A | 12/1999 | Greenberger et al. | |
| 6,048,721 A | 4/2000 | Armstrong et al. | |
| 6,096,532 A | 8/2000 | Armstrong et al. | |
| 6,110,212 A | 8/2000 | Gregory | |
| 6,121,042 A | 9/2000 | Peterson et al. | |
| 6,174,719 B1 | 1/2001 | Elizondo et al. | |
| 6,228,635 B1 | 5/2001 | Armstrong et al. | |
| 6,238,908 B1 | 5/2001 | Armstrong et al. | |
| 6,416,995 B1 | 7/2002 | Wolfinbarger | |
| 7,270,996 B2 * | 9/2007 | Cannon et al. | 435/293.1 |
| 2002/0055166 A1 | 5/2002 | Cannon et al. | |
| 2002/0115208 A1 | 8/2002 | Mitchell et al. | |

FOREIGN PATENT DOCUMENTS

WO　　WO 02/28996　　4/2002

OTHER PUBLICATIONS

"A Completely Biological Tissue-Engineered Human Blood Vessel", by Nicolas L'Heureux, et al., The FASEB Journal, vol. 12, Jan. 1998, pp. 47-56.

"Functional Arteries Grown in Vitro", by L.E. Niklason, et al., Science, vol. 284, Apr. 16, 1999, pp. 489-493.

"Liposuction-Derived Human Fat Used for Vascular Graft Sodding Contains Endothelial Cells and Not Mesothelial Cells as the Major Cell Type", by Stuart K. Williams, PhD., et al., Journal of Vascular Surgery, vol. 19, No. 5, May 1994, pp. 916-923.

"Long-Term Results of Femorotibial Bypass With Vein or Polytetrafluoroethylene", R.D. Sayers, et al., British Journal of Surgery, vol. 85, 1998, pp. 934-938.

"Morphologic and Mechanical Characteristics of Engineered Bovine Arteries", Laura E. Niklason, MD, et al., Journal of Vascular Surgery, vol. 33, No. 3, Mar. 2001, pp. 628-638.

"Optimizing Seeding and Culture Methods to Engineer Smooth Muscle Tissue on Biodegradable Polymer Matrices", by Byung-Soo Kim, et al., Biotechnology and Bioengineering, vol. 57, No. 1, Jan. 5, 1998, pp. 46-54.

"Remodeling of Autologous Saphenous Vein Grafts", by Yi Shi, MD, et al., Circulation, vol. 95, No. 12, Jun. 17, 1997, pp. 2684-2693.

"Scaffolds for Engineering Smooth Muscle Under Cyclic Mechanical Strain Conditions", by Byung-Soo Kim, et al., Journal of Biomechanical Engineering, vol. 122, Jun. 2000, pp. 210-215.

The Role of Crosslinking in Modification of the Immune Response Elicited Against Xenogenic Vascular Acellular Matrices, by David W. Courtman, et al., Journal of Biomed. Mater. Res., vol. 55, 2001, pp. 576-586.

"Use of Cardiac Procedures and Outcomes in Elderly Patients with Myocardial Infarction in the United States and Canada", by Jack V. Tu, MD, et al., The New England Journal of Medicine, vol. 336, No. 21, May 22, 1997 pp. 1500-1505.

Abstract, "Re-endothelialization of porcine derived elastin heterografts using porcine aortic endothelial cells, pulsatile perfusion, and controlled shear stress conditions." Kenton W. Gregory et al., Poster presented at Sixth World Biomaterials Congress, Kamuela, HI, May, 2000.

"Elastin As a Matrix for Vascular Cell Repopulation for Stent Coverings and Conduits", Abstract presented at Elastin 2001 Conference, Reims, France, Jul. 2001.

*Aastrom Biosciences, Inc.*, Annual Report 2001.

*Cell Manufacturing Instruments*, BioVest, http://www.biovest.com/cmi.html, Aug. 22, 2001.

Synthecon, Inc.—Products, http://www.synthecon.com/products.shtml, Aug. 22, 2001.

*FiberCell™ Hollow Fiber Cell Culture Systems*, FiberCell Systems, Inc., Hollow Fiber Cell Culture Technology, wysiwyg://129/http://www.fibercellsystems.com/about.htm, Aug. 22, 2001.

FiberCell Systems Inc., Hollow Fiber Cell Culture Technology, Product Specifications, wysiwyg://136/http://www.fibercellsystems.com/specifications/htm, Aug. 22, 2001.

*CELLMAX® Artificial Capillary Cell Culture Systems*, Cellco Cellmax, http://www.spectrapor.com/cellco/cellmax.html, Aug. 22, 2001.

International Search Report in Application PCT/US03/09584 mailed Jul. 14, 2003.

International Search Report in Application PCT/US01/30630 mailed Feb. 13, 2002.

* cited by examiner

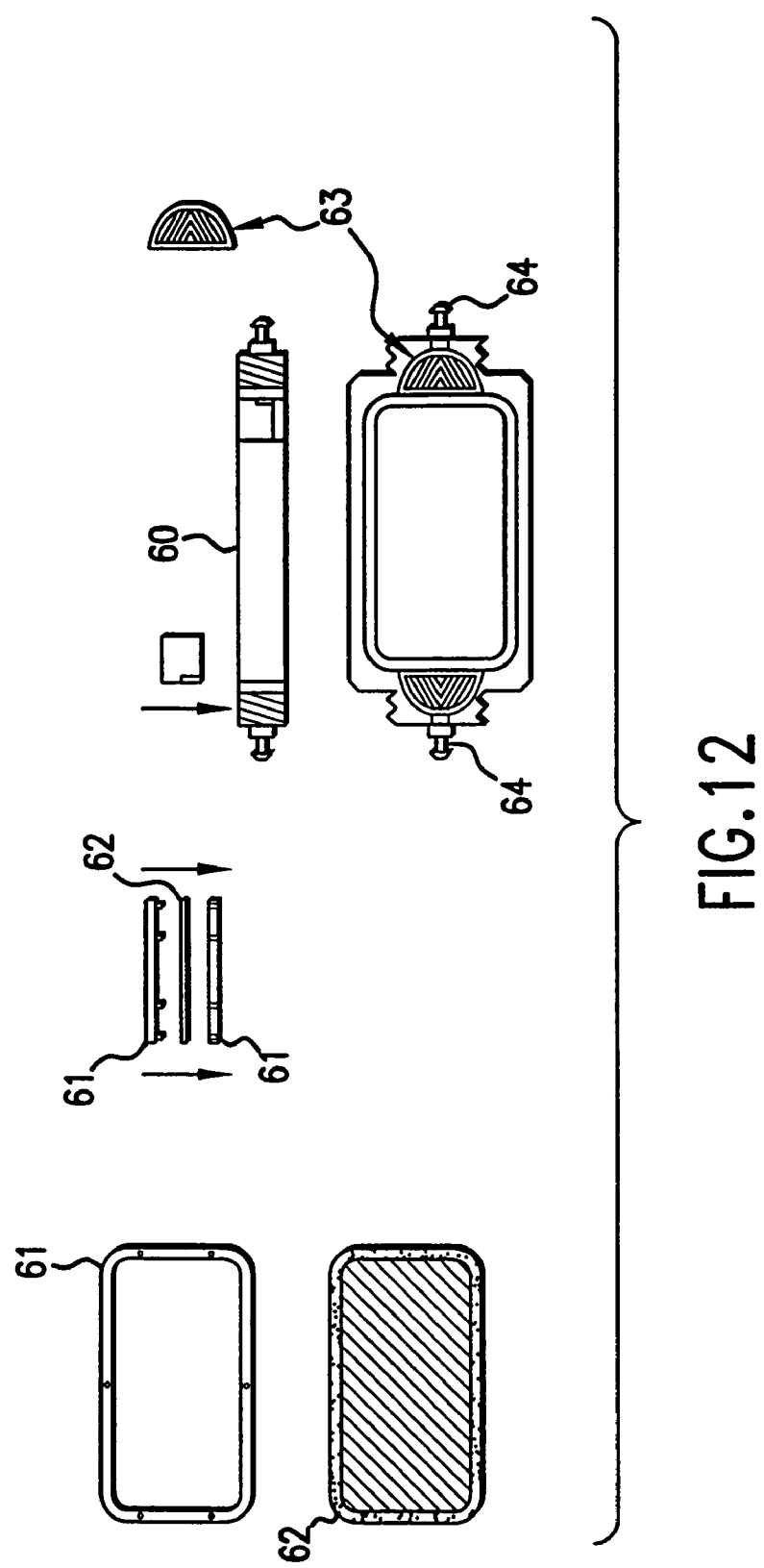

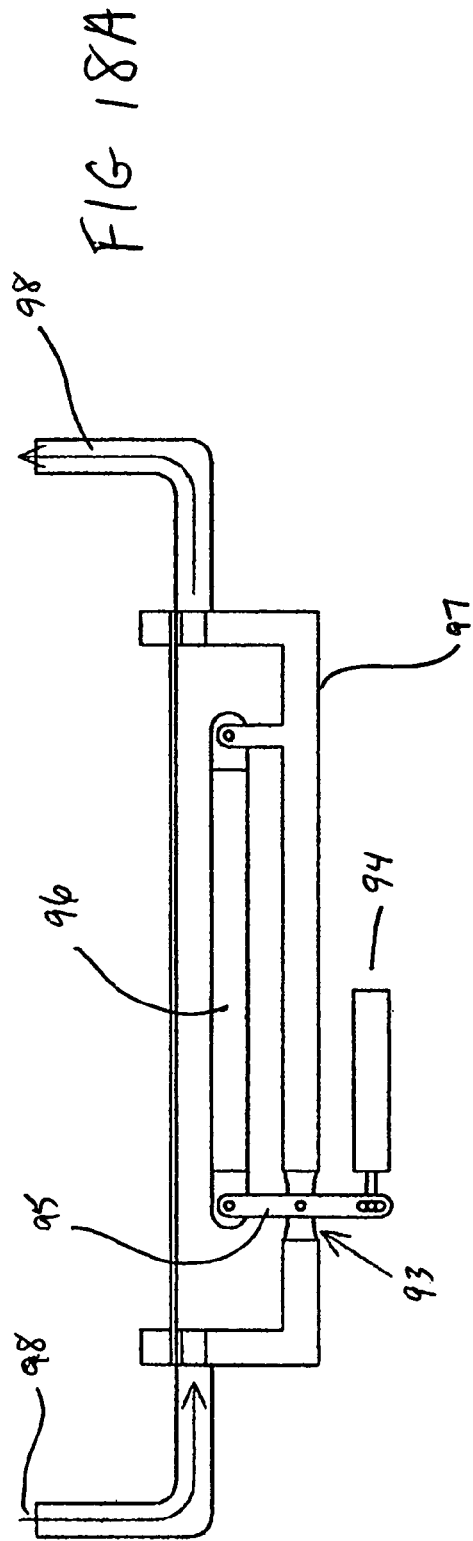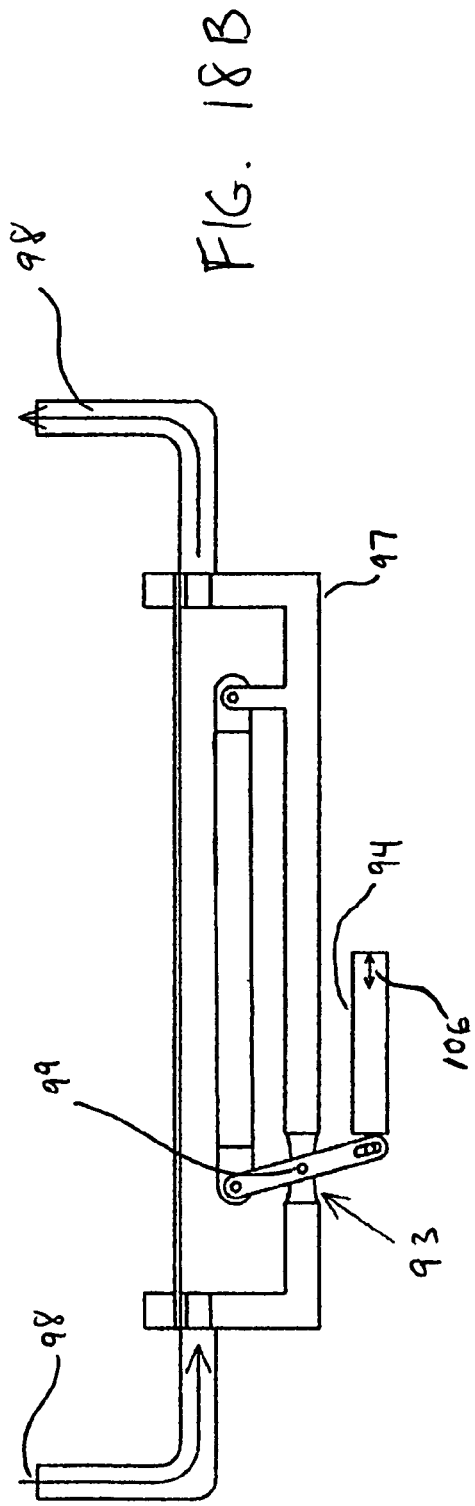

AUTOMATED BIOCULTURE AND BIOCULTURE EXPERIMENTS SYSTEM

This application is a divisional application of U.S. patent application Ser. No. 10/109,712, filed Apr. 1, 2002, now abandoned, which is a continuation-in-part of U.S. patent application Ser. No. 09/967,995, filed Oct. 2, 2001 now U.S. Pat. No. 7,270,996.

FIELD OF THE INVENTION

The field of the invention is automated cell culture systems, cell culture growth chambers and automated sampling systems.

BACKGROUND OF THE INVENTION

Cell culture has been utilized for many years in life science research in an effort to better understand and manipulate the cellular component of living systems. Cells are typically grown in a static environment, on petri dishes or flasks, in which each experiment uses a stream of sterile, disposable products. These cell culture methods are very labor-intensive especially when a large number of studies need to be performed.

Traditional cell culture systems depend on controlled environments for cell maintenance, growth, expansion, and testing. Typical cell culture laboratories include laminar flow hoods, water-jacketed incubators, controlled access by gowned personnel, and periodic sterilization procedures to decontaminate laboratory surfaces. Personnel require extensive training in sterile techniques to avoid contamination of containers and cell transfer devices through contact with non-sterile materials. Despite these measures, outbreaks of contamination in traditional cell culture laboratories, e.g., fungus or bacterial contamination, commonly occur, often with the impact of compromising weeks of research and halting operations for days or weeks.

Trained technicians under a sterile, laminar flow hood typically perform cell culture. Cells are grown in flasks or bioreactors and maintained in incubators that provide the requisite thermal and gas environment. Cultures are removed from incubators and transported to a sterile hood for processing. Cells can be harmed when removed from their thermal and gas environment. The frequent transport and manipulation of the culture represents an opportunity for contamination from a single bacterium that can cause weeks of work to be wasted. The nutrient cell culture medium includes a color indicator that is visually inspected by the technician on a daily basis, at a minimum. When the color is deemed to indicate that the pH is deviating from a healthy range, the cells are removed from the incubator, the old media is manually removed and fresh media is injected. This process is adequate at best.

Perfusion systems provide a three-dimensional cell culture environment that reproduces critical aspects of the dynamic in vivo environment. In vitro perfusion systems allow tissue-engineered cells to develop and organize as if inside the body. Biotechnology companies, universities, and research institutes are attempting to develop complex tissue replacements including liver, pancreas, and blood vessels, among others. These complex tissue products require advanced biochamber perfusion systems that are capable of mimicking in vivo development dependent stimulation for optimal tissue development. A perfusion cell culture system's primary purpose is to provide a pump that will continuously re-circulate medium. Standard experiment manipulations, such as media replacement (when it is no longer at the proper pH), cell and media sampling, and fluid injections, are traditionally performed by a laboratory technician in a sterile hood. In an age where genetically engineered products will be FDA approved and drug compound costs are hundreds of millions of dollars, the traditional way of performing cell culture is no longer acceptable.

One critical issue to be addressed in any cell culture application involves precision reproducibility and the elimination of site-to-site and batch-to-batch differences so that cell products and experiments will be consistent in different biochambers or different physical locations. This is particularly difficult to accomplish when culture viability is determined solely on subjective visual cues, i.e., medium color and visualization under a microscope.

In a purely manual environment, quality control is accomplished by selecting qualified personnel, providing them with extensive training, and developing a system of standard operating procedures and documentation. In an automated environment, the principles of process validation are used to demonstrate that the process is precise, reliably consistent, and capable of meeting specifications. The principles of statistical process control are then implemented to monitor the process to assure consistent conformance to specifications.

The particular physical and biological requirements for the growth and modification of cells and tissues of interest vary. However, two key components are necessary for cell and/or tissue culture: cells that are capable of replicating and potentially differentiating and an in vitro system containing biocompatible materials that provide for the physiological requirements for the cells to remain viable, proliferate, differentiate, and/or organize into desired tissue structures. These requirements include temperature, pH, surfaces appropriate for cell attachment, nutrient exchange, waste removal, and oxygenation. These systems should be automated and amenable for routine use by the thousands of research laboratories, universities, tissue engineering companies, hospitals, and clinics that perform research requiring consistent and reliable results and also those that serve patients intended to benefit from transplantation cells and tissues in native or genetically altered form without adversely affecting product quality and, particularly, product sterility.

Cell and organ transplantation therapy to date has typically relied on the clinical facility to handle and process cells or tissues through the use of laboratory products and processes governed to varying degrees by standard operating procedures and with varying regulatory authority involvement. The procedures to date, however, generally have not required extensive manipulation of the cells or tissue beyond providing short term storage or containment, or in some cases, cryopreservation. With the addition of steps that require the actual growth and production of cells or tissues for transplantation, medium replacement, sampling, injections of drug/compound dosing, physiologic and set-point monitoring, and quality assurance data collection, there are many considerations that need to be addressed in order to achieve a reliable and clinically safe process. This issue is the same regardless of whether the cell production is occurring at the patient care location, as might be the case for the production of cells for a stem cell transplant, or at a distant manufacturing site, as might be the case for organ and tissue engineering applications.

Platform-operated culture systems, typically referred to as bioreactors, have been commercially available. Of the different bioreactors used for mammalian cell culture, most have been designed to allow for the production of high density cultures of a single cell type. Typical application of these high density systems is to produce a conditioned medium produced by the cells. This is the case, for example, with hybridoma production of monoclonal antibodies and with packaging cell lines for viral vector production. These applications differ, however, from applications in which the end-product is the harvested tissue or cells themselves. While traditional bioreactors can provide some economies of labor and minimization of the potential for mid-process contamination, the set-up and harvest procedures involve labor requirements and open processing steps, which require laminar flow hood operation (such as manual media sampling to monitor cell growth). Some bioreactors are sold as large benchtop environmental containment chambers to house the various individual components that must be manually assembled and primed. Additionally, many bioreactor designs impede the successful recovery of expanded cells and tissues and also can limit mid-procedure access to cells for purposes of process monitoring. Many require the destruction of the bioreactor during the harvesting process.

It should therefore be appreciated that within tissue engineering companies, cellular therapeutic companies, research institutions, and pharmaceutical discovery companies there is a need for an automated cell and tissue culture system that can maintain and grow selected biological cells and tissues without being subject to many of the foregoing deficiencies. There also is a need for a lower cost, smaller, automated research and development culture system which will improve the quality of research and cell production and provide a more exact model for drug screening.

SUMMARY OF THE INVENTION

The present invention provides a precision bioculture support system, including a cell culture apparatus for use within an incubator. The apparatus preferably includes at least one media flowpath assembly cartridge having an outer shell or housing and affixed thereto, a pump, at least one valve adapted to prevent or divert media flow, a control interface, and a disposable sterile media perfusion flowpath loop. The media perfusion loop is removably attachable to the outer shell without breaching flowpath sterility, and contains, in fluid communication, at least one biochamber, a tubing in contact with the pump, at least one tubing in contact with the valve, a gas permeable membrane exposed to ambient air, and a media reservoir. In a preferred embodiment, each cartridge has a control interface and battery pack or other power source for stand alone operation. In another preferred embodiment, the apparatus further includes an incubator rack that is removably integratable with a plurality of flowpath assembly cartridges without breaching flowpath sterility and while maintaining flowpath indentity.

Another embodiment of the invention provides an incubator rack for supporting a plurality of flowpath assembly cartridges. The rack includes, in one embodiment, a plurality of grooves each adapted to support a flowpath cartridge, a plurality of data interface connections for transmitting data between the rack and the cartridges, and a control interface for communication with an external computer or other data storage/user interface device. The rack provides structural alignment and access to each of the resident cartridges and biochambers contained therein. The access area and alignment structure allow for a variety of interfaces through the access port including, for example, video microscopy, mechanical stimulation, and growth and turbidity interrogations.

The invention further provides an automated sampling capability having a fluidic pump for transporting a carrier fluid, a check valve for diverting an aliquot of sample from a perfusion loop, and a means for maintaining the sterility of the carrier fluid. The pump, filter, and check valve are connected in series by tubing or other means of sterile fluid routing for transporting the carrier fluid and the diverted sample from the check valve to a sample collection device or analysis instrument. The sample collection device connection may include a heat source or other means to re-sterilize the connection. In a preferred embodiment, the fluid routing system is disposable to limit opportunities for cross-contamination.

The invention further provides a biochamber which is convertible for use in static cell culture or in a perfusion apparatus. The biochamber includes a first chamber, a cover, a seal rendering the first chamber removably connectable to the cover and preventing contamination of the cell culture within the biochamber, and providing for an insert positioned between the first chamber and the cover, thereby forming a second chamber.

Additional features and advantages of the invention will be set forth in the description which follows and will be apparent from the description or may be learned by practice of the invention.

BRIEF DESCRIPTION OF THE DRAWINGS

FIG. 12 illustrates separate components of an alternate biochamber embodiment.

FIGS. 18A and B illustrate a biochamber providing tensile mechanical stimulation to a tissue specimen.

DETAILED DESCRIPTION OF THE INVENTION

Reference will now be made in detail to the presently preferred embodiments of the invention which serve to explain the principles of the invention. It is to be understood that the application of the teachings of the present invention to a specific problem or environment will be within the capabilities of one having ordinary skill in the art in light of the teachings contained herein.

The present invention provides an automated precision cell culture system which includes one or a plurality of perfusion loop flowpath cartridges that can be placed in an optional rack or docking station which fits into an incubator. The incubator provides the appropriate gas and thermal environment for culturing the cells as each perfusion loop contains a means for passive diffusion of air from the incubator environment. The system provides for parallel processing and optimization through continuous set point maintenance of individual cell culture parameters as well as automated sampling and injection. The invention further provides a biochamber which is convertible for use as a static cell culture device or in a perfusion loop flowpath cartridge.

As used herein, "cell culture" means growth, maintenance, differentiation, transfection, or propagation of cells, tissues, or their products.

As used herein, "integratable" means parts or components which are capable of being joined together for operation as a unit for one or more data transfer or other functions.

As used herein, "without breaching flowpath sterility" refers to the closed nature of the perfusion loop which remains intact during various manipulations or movements such that each flowpath assembly perfusion loop can be connected to a cartridge housing, which in turn can be connected to a rack or docking station, disconnected and then reconnected without exposing the internal surfaces of the flowpath to environmental contaminants and without the components of the perfusion loop flowpath losing fluid communication with one another. Thus, the loop itself is preferably a disposable, unitized system that can be removed from the cartridge's outer shell without its components losing fluid communication with one another. Moreover, an individual perfusion loop can be moved or carried throughout a laboratory or other facility, or to a separate lab or facility, as desired for separate testing or analyses while its contents remain sterile.

Figure 1:
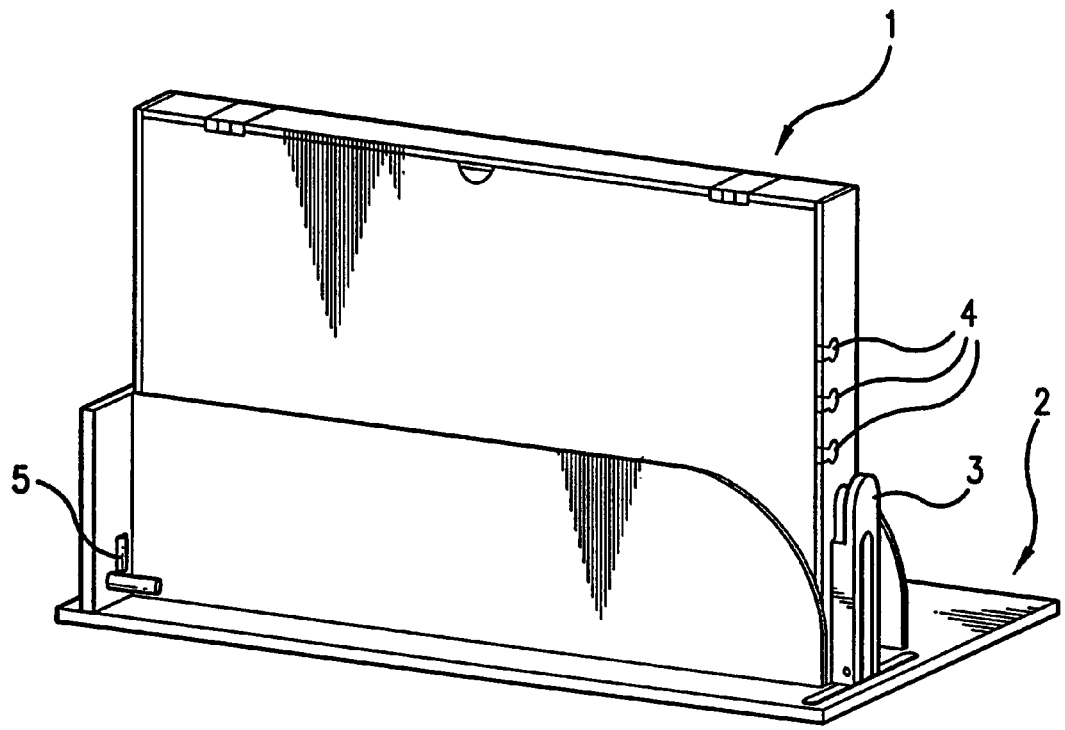
FIG. 1 depicts a media flowpath assembly cartridge and incubator rack in accordance with the invention.

Referring now to FIG. 1, the present invention provides one or a plurality of media flowpath assembly cartridges, 1, which each can be placed into docking station or rack, 2, which can then be placed into a laboratory incubator. The incubator may be any incubating device, and may be located in a laboratory, a manufacturing facility, or any clinical or other setting in which cell culture via incubation is desired. The incubator preferably maintains a controlled environment of about 5% $CO_2$ and about 20% $O_2$ and controlled temperature and relative humidity, although any environment may be used and selected by one of ordinary skill depending on the particular end use application, given the teachings herein. The incubator environment is typically separately controlled, while the automated culture system of the invention is preferably controlled by an external PC or control pod for integration of individual flowpath assembly cartridges and system control through a docking station interface, as described in detail below. The control pod is a user-interface with embedded microprocessors and a graphical user interface, but is not necessarily a PC.

The illustrated embodiment of FIG. 1 includes an optional lever 3 for facilitating the cartridge's integration and removal from the rack. In alternate embodiments, a latch or other capture device may be used. The illustrated embodiment also includes optional access ports 4 to accommodate injection or sampling of fluid. One or more connections 5 may also be included for connecting power sources and computer control and data transfer cables.

Figure 2:
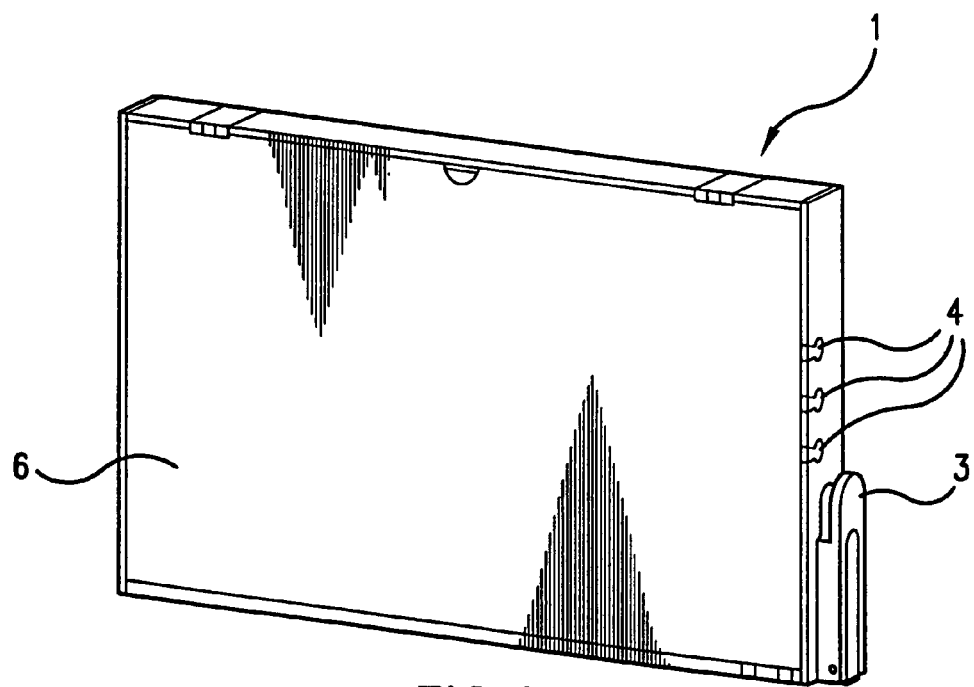
FIG. 2 depicts a media flowpath assembly cartridge in accordance with the invention.
Figure 3:
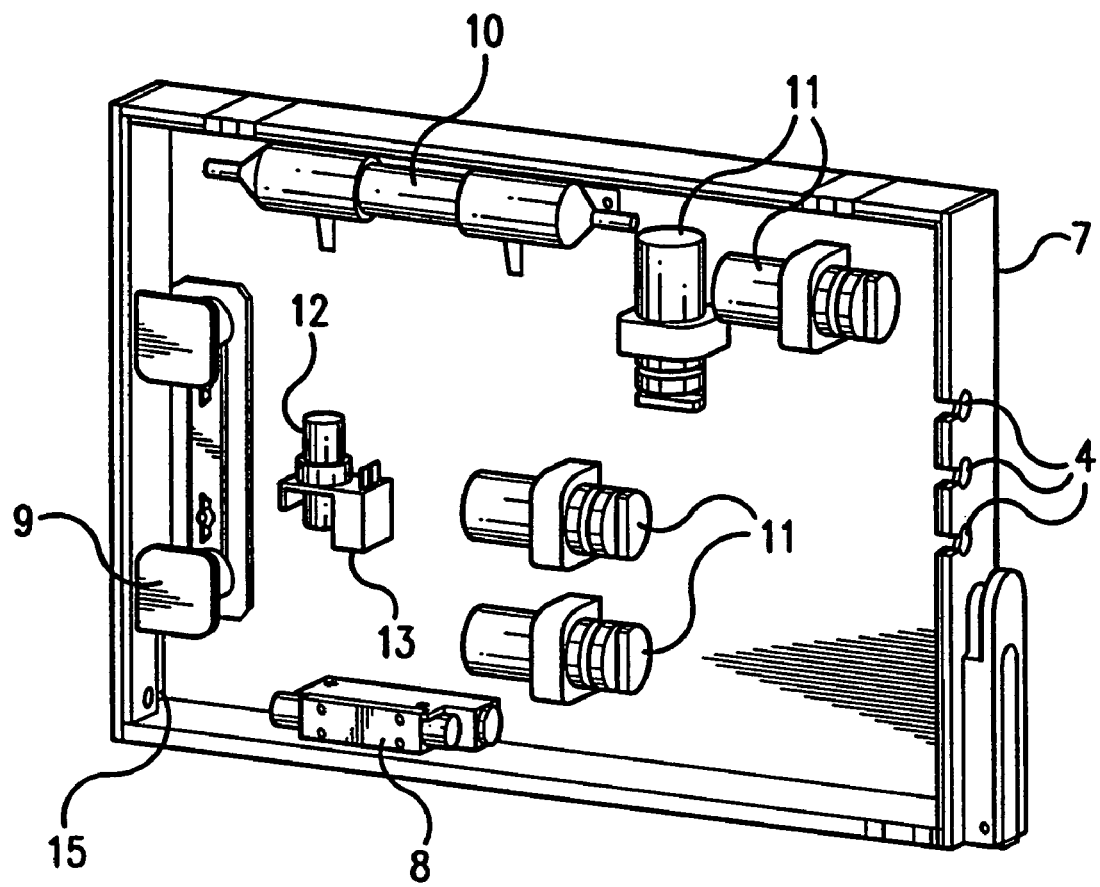
FIG. 3 shows the outer shell of an exemplary cartridge and its fixed components.

FIG. 2 illustrates an embodiment of the invention in which an individual flowpath assembly cartridge is not attached to a rack. In this illustrated embodiment, an optional cover 6 encloses the cartridge's inner components. The cover may be removable and may be connected to the cartridge's outer shell by a hinge. With reference now to FIG. 3, a cartridge outer shell or housing 7 provides physical support for the internal components. The embodiment shown in FIG. 3 illustrates internal hardware components of a preferred cartridge outer shell or housing, including a pump 8, an optional oxygenator bracket 9, a biochamber 10, valves for diverting media flow 11, a flow cell or drip chamber 12, a noninvasive sensor 13, a series of access ports 4, an optional air pump for sample routing 0.1 micron filtered air (not shown in FIG. 3), and an interface 15 for interfacing with a connection located on the rack or with a separate power source. The flow cell or drip chamber may be combined with a noninvasive sensor, for example a pH sensor, to form a single component. In an alternate embodiment, interface 15 may provide a connection for a computer cable for control and data transfer. In another alternate embodiment, interface 15 may provide fluid connection downstream to an in-line analyzer. The in-line analyzer may provide data on, for example, cell metabolic activity. Many such in-line analyzers are suitable for use in the present invention.

Figure 4:
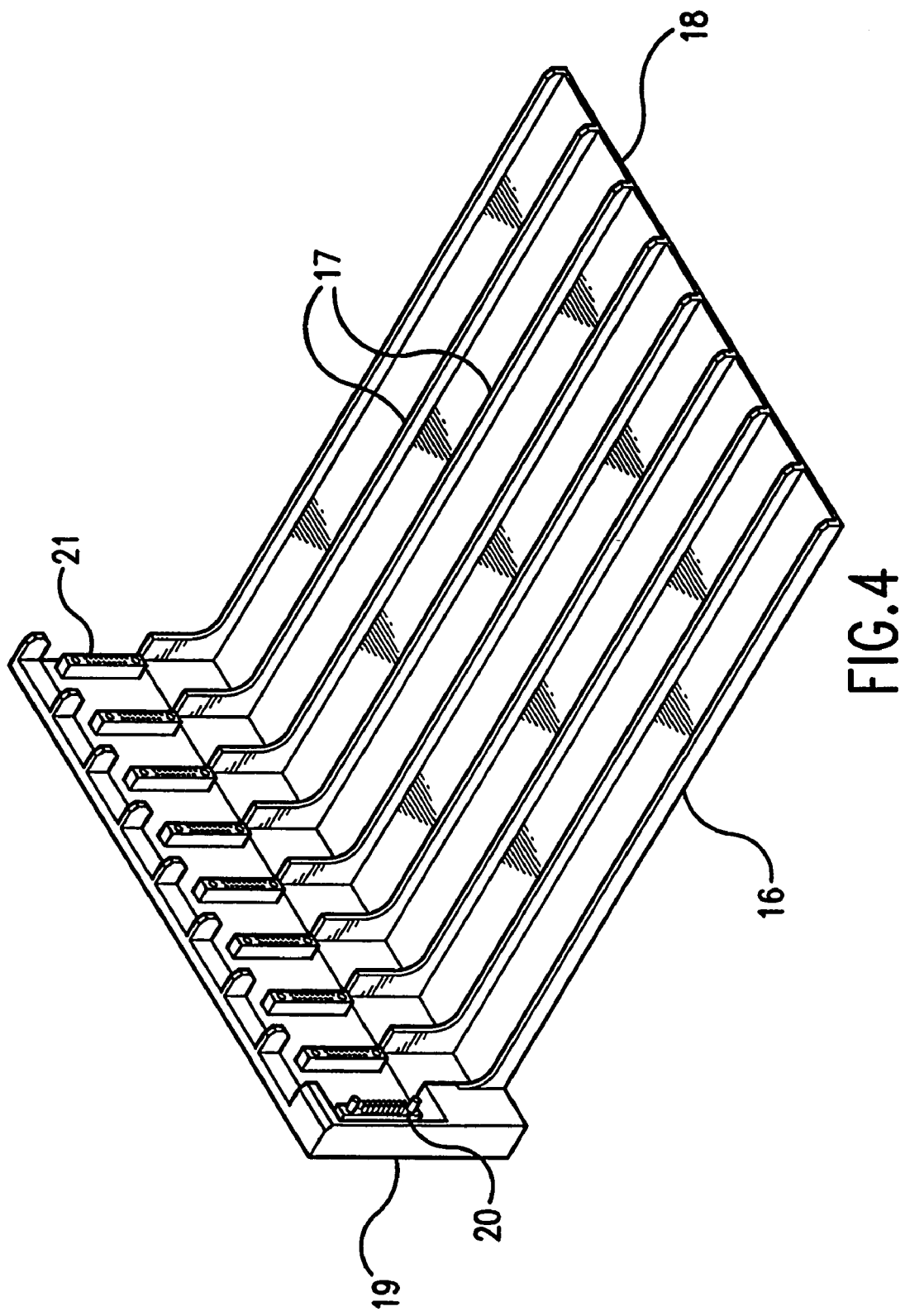
FIG. 4 shows an incubator rack in accordance with the invention.

The incubator rack operates as a docking station for one or preferably multiple cartridges when they are positioned within an incubator during operation of the cell culture system. The rack or docking station is preferably fabricated from a plastic material and may be manufactured by, for example, injection molding. Referring to FIG. 4, in one embodiment the rack has a horizontal base 16 and a series of vertical dividers 17 forming grooves, or tracks 18 for guiding the insertion of and supporting each flowpath assembly cartridge. In one embodiment, the vertical dividers provide a small space between each docked cartridge and its adjacent or neighboring cartridge. The rack may also provide orthogonal support via a vertical wall 19 preferably in the rear of the rack. The rack may also have at least one connector 20 and 21, preferably in the rear and affixed to the vertical wall, for conveying power from a power source and for communication with an external computer. Connectors may also be present for attaching a power or communication cable to a single cartridge or to multiple cartridges operating within the same rack. A series of connectors may optionally be attached to a circuit board laid into a groove in the rear plane of the rack (not shown). The rack may also include a fan for circulating air within the incubator or a vibration isolation and damping system. To allow access to the biochambers aligned in the docking station, an access window may be provided, for example, below the horizontal plane of the biochamber(s). The window allows interface with video imaging systems, mechanical stimulation systems or other devices.

To increase portability of a fully loaded rack, an open box structure can be employed which further protects the front section and secures the cartridges for transporting within the rack as a unit. In the embodiment shown in FIG. 4, the rack accommodates eight cartridges. An incubating device suitable for use in accordance with the present invention can accommodate a rack adapted to hold any desired number of cartridges. The rack may thus be manufactured to include as many slots or tracks as can fit into a standard laboratory incubator or other suitable incubating device. A common laboratory incubator will readily support up to ten cartridges or more on one shelf.

A lever action removal mechanism may be included to overcome resistance of the electrical connectors to disengagement and thus facilitate removal of each cartridge from the rack. In another embodiment, an indicator illuminates when a cartridge is properly connected to the electrical connectors or when a cartridge is not receiving power. The indicator is preferably an LED. In a still further embodiment, a battery power source is included on or in the cartridge to provide back up power and power for when the cartridge is transported or otherwise removed from the rack. A handle may be located on each cartridge housing to facilitate its removal from the rack. Such handles can include an indentation for grasping, which may be located in various locations, preferably the top, right-hand side, a foldaway handle, or any other mechanism for facilitating manual transfer and portability of each cartridge. The cartridge's outer shell is preferably made of plastic and may be formed by injection molding. The cartridge may also include a display or control panel. The cartridge may also include a circuit board in one of numerous locations. A preferable location is on or embedded in the back plane of the cartridge's outer shell. In an alternate embodiment, a fold out stand on the bottom plane of the cartridge outer shell may be included. The stand would allow the user to place the cartridge on a desktop once the flow path is inserted and is an aid to keep the cartridge in a vertical position during some phases of sterile processing in the sterile hood. Prior to inserting the cartridge into the rack, the stand can be rotated 90 degrees into a tucked away position. Any other stand or suitable mechanism capable of providing support on a table or bench, or other horizontal surface for an individual cartridge can be used, if desired.

In one embodiment, cartridges may be integrated such that two or more flowpaths are in fluid connection with each other for conducting experiments. This embodiment is advantageous when, for example, increased fluid volume, increased cell volume, or cell co-culture is desired. Cell co-culture includes culturing a different cell type in each cartridge. In an alternate embodiment, larger cartridges with increased biochamber and media supply are accommodated for large scale cell and/or tissue culture.

Figure 5:
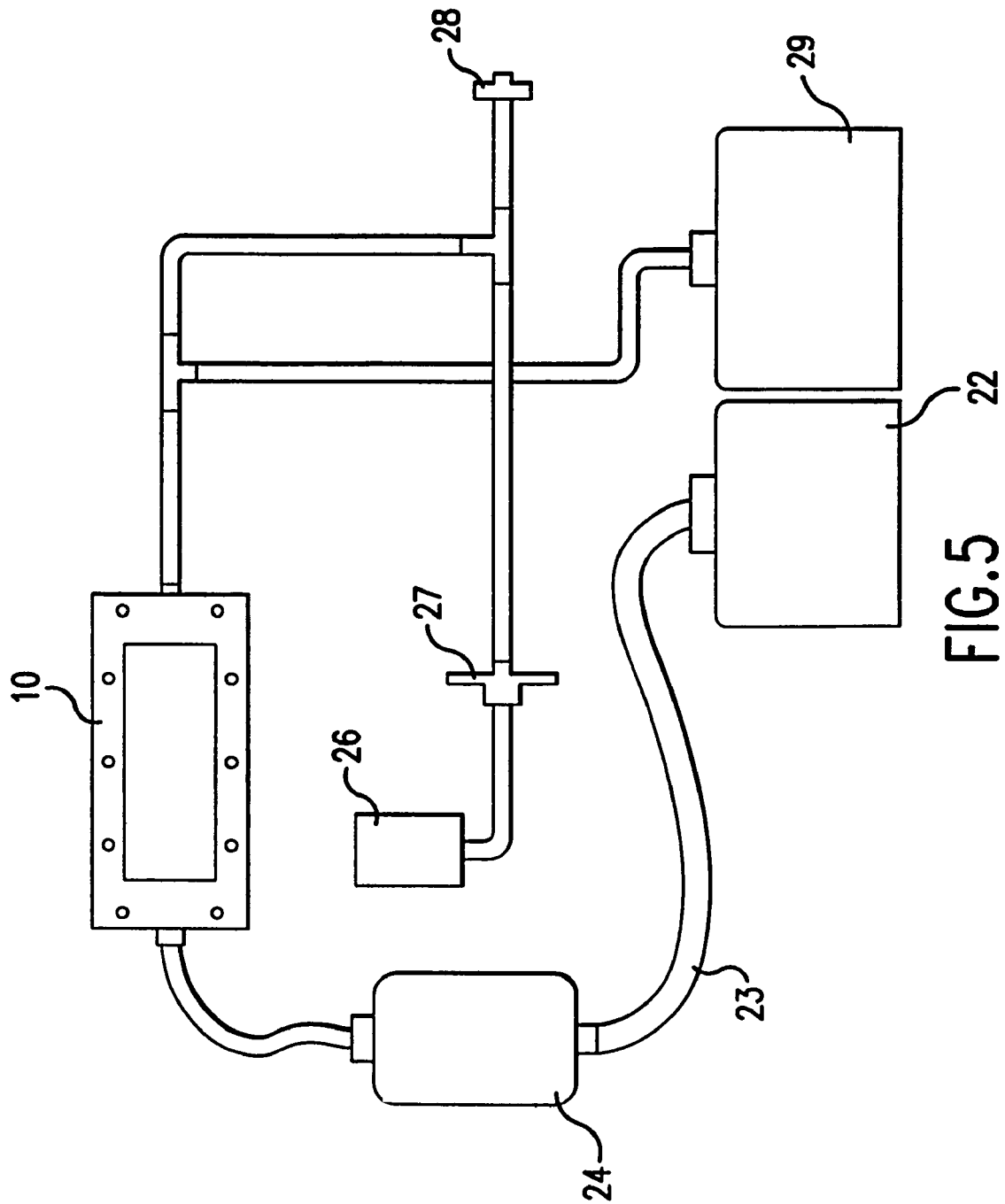
FIG. 5 shows a unitized, disposable flowpath perfusion loop in accordance with the invention.

The invention further provides a unitized, disposable sterile media perfusion loop flowpath, which is removably attachable to the outer shell or housing of the cartridge without breaching flowpath sterility. The perfusion loop is preferably a continuous flow perfusion loop, but can also function as a single pass perfusion loop. In an alternate embodiment, the perfusion loop is a single pass perfusion loop. The loop is preferably removable from the cartridge housing as a single disposable unit. FIG. 5 illustrates one embodiment of a unitized perfusion loop according to the invention. In FIG. 5, the loop is not connected to a cartridge. As shown in the embodiment of FIG. 5, the media perfusion loop or flowpath includes a media reservoir 22, tubing 23, an oxygenator 24, a biochamber or bioreactor 10, an interface to accommodate an air supply 26 for sample removal, a filter 27 for sterilizing air from the air supply, a sampling interface 28, and a waste reservoir 29 (injection and sample reservoirs not shown in this Fig.). In an alternate embodiment, the flowpath includes an interface for connection with an analyzer. The oxygenator 24 is preferably a passive diffusion oxygenator. The oxygenator may comprise any gas permeable surface. In an alternate embodiment, the oxygenator is a diffusion membrane positioned, for example, over a valve manifold. The valve manifold is potentially a series of cam-like devices that rotate into a variety of positions. As they rotate, they deform the membrane in various positions such that the position of the overlay provides for fluid diffusion into predetermined directions through the etched plastic below. This membrane also allows for the diffusion of gas and may take the place of a separate oxygenator. In this embodiment, tubing is only used at the biochamber interface and may or may not be utilized at the fluid reservoir interfaces. In another alternate embodiment, the oxygenator is a diffusion membrane positioned over the biochamber. Alternatively, the oxygenator may be a hollow fiber for accommodating forced gas. Additionally, in alternate embodiments, any or all of the preceding gas exchange interfaces may use active mass transport of gas across the interface rather than passive diffusional transport.

In an alternate embodiment, more than one biochamber or bioreactor is included in a single flowpath for increasing cell volume or to provide co-culturing. The biochambers may be connected in series or in parallel. Waste contained in the waste reservoir 29 may include spent media, cellular byproducts, discarded cells, or any other component that enters the waste reservoir 29 through the media perfusion loop. Sampling interface 28 may be any suitable connection or surface forming a boundary through which a sample may be extracted from the perfusion loop while eliminating or minimizing any potential breach in flowpath sterility. Extraction may be manual or automated. The sampling interface may, for example, be a silicon injection site or a luer connection.

Figure 6:
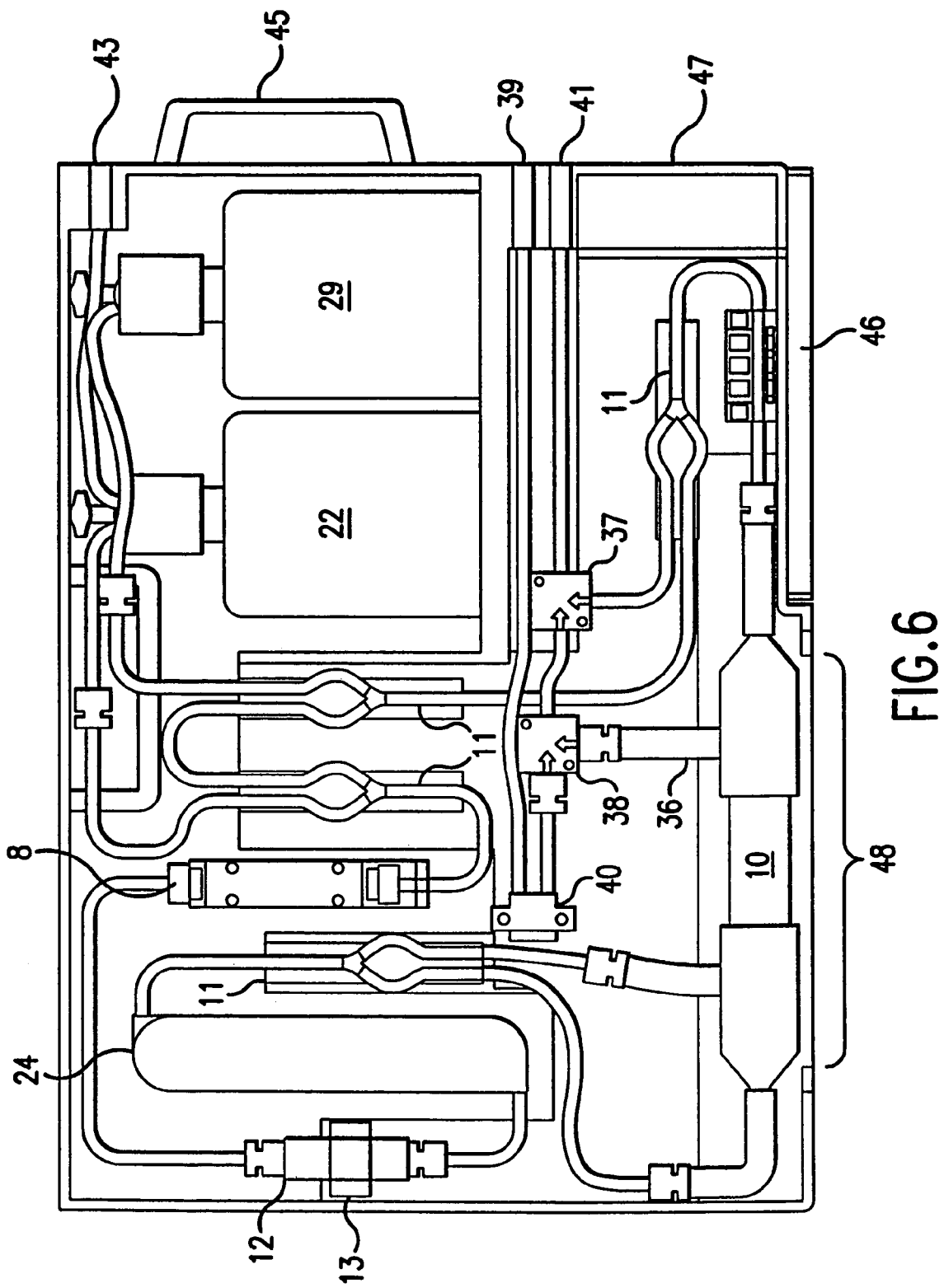
FIG. 6 is a schematic illustrating a cartridge and flowpath assembly, including an integrated automated sampling apparatus.
Figure 7:
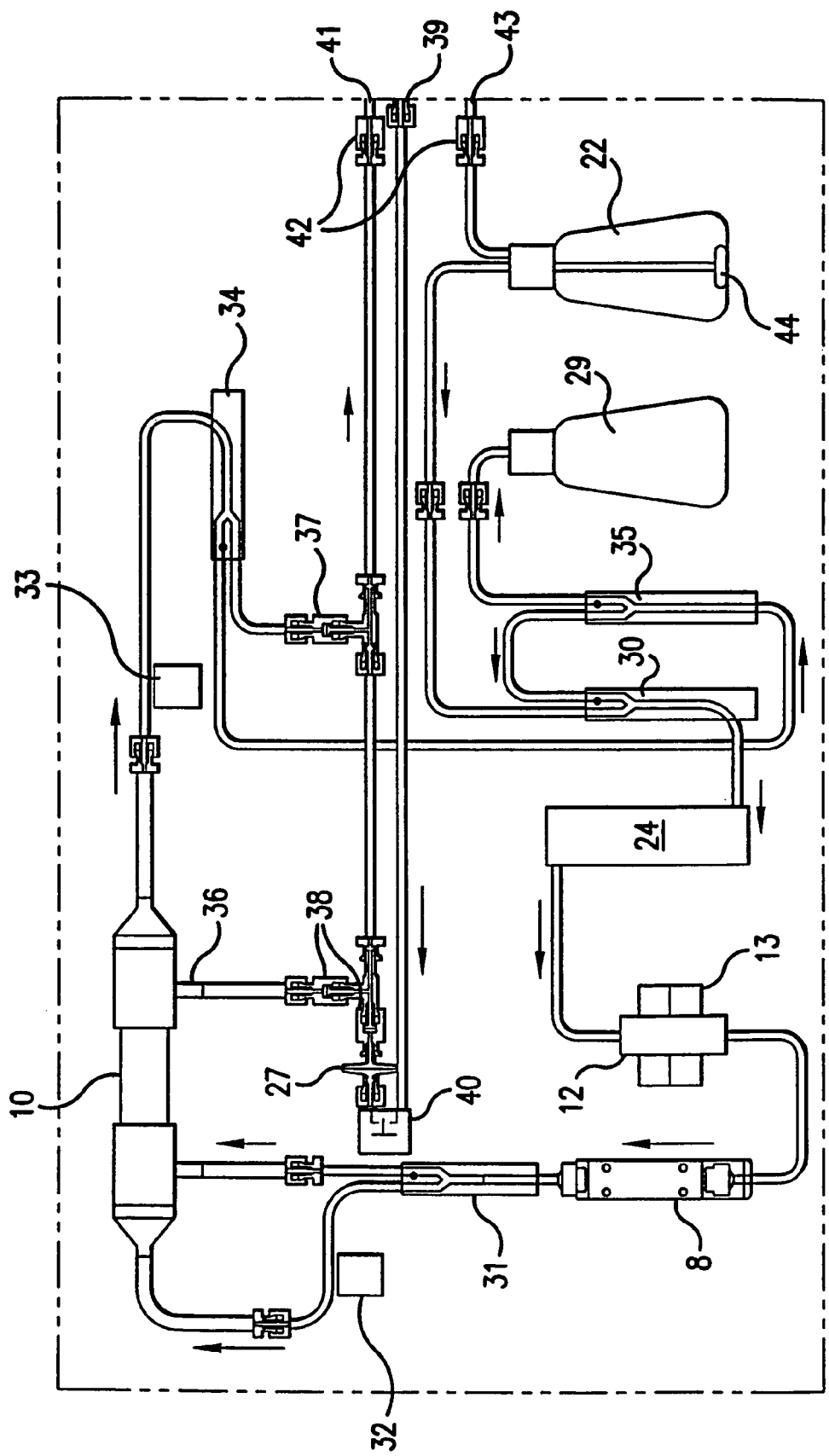
FIG. 7 is a schematic illustrating an alternate embodiment of a cartridge and flowpath assembly.
Figure 8:
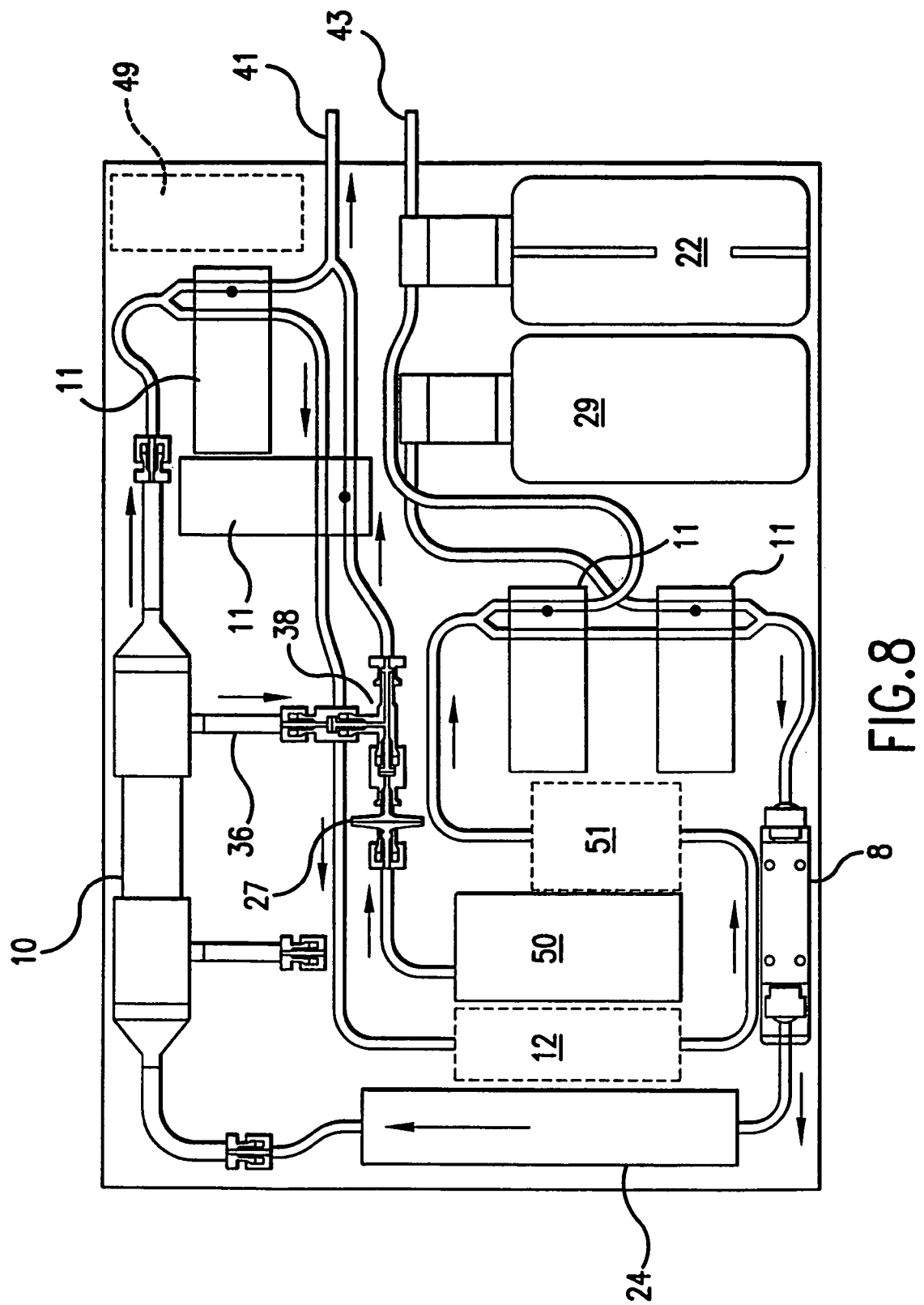
FIG. 8 is a schematic illustrating a further alternate embodiment of a cartridge and flowpath assembly.

FIGS. 6, 7, and 8 illustrate alternative embodiments of a media perfusion loop or flowpath arranged within a cartridge housing in accordance with the present invention. Referring to FIG. 7, during operation, media contained in the media reservoir 22 travels via tubing through a tubing section in contact with a first valve 30 which diverts a portion of the media to oxygenator 24. In the illustrated embodiment, the diverted media then travels through a flow cell 12 which is removably attachable to a noninvasive sensor 13. In a preferred embodiment, the flow cell comprises a drip chamber. As used herein, "noninvasive" means that the sensor operates without invading or interfering with the sterility of the perfusion loop. Noninvasive sensor 13 is preferably a pH sensor or combination pH sensor/drip chamber. The flow cell provides a selective barrier membrane which prevents proteins and other substances in the media from interfering with the detection signal. The membrane may allow for easy transfer of hydrogen ions across the membrane to the detection path of the sensor. The pH sensor preferably includes LEDs and photodetectors for measuring light transmission through cell culture media. The noninvasive sensor may be an oxygen sensor or any other analyzer suitable for use in the present invention.

In FIG. 7, the media then travels through a tubing section in contact with a pump 8, then through a tubing section in contact with a second valve 31, which diverts a portion of the flow either directly to biochamber 10, or first through tubing which subjects the circulating media to a first noninvasive oxygen sensor 32 then to biochamber 10. In the illustrated embodiment, the media then flows from the biochamber 10 past a second noninvasive oxygen sensor 33 and through a tubing section in contact with a third valve 34. In the illustrated embodiment, valve 34 may divert the flow to a tubing section in contact with a fourth valve 35, which in turn diverts the flow either back through tubing in contact with first valve 30 for recirculation or to waste reservoir 29. The first, second, third, or fourth valves may be pinch valves. Alternatively, the first second, third, or fourth valves may be a diverter valve routing manifold including means for flow reversal. As illustrated, flow may also be diverted from biochamber 10, through valve 34, and through first check valve 37 integrated with a sampling apparatus for sampling the contents of the biochamber. Alternatively, flow may be diverted from biochamber 10 through side sampling port 36 and through a second check valve 38 integrated with a sampling apparatus. The tubing section in contact with the pump or valves may form a diaphragm. In alternate embodiments, the perfusion loop can include additional diverter valves and Y selector flowpath routings for cell sampling, intra-chamber media sampling, reverse flow, and numerous other applications for which diversion of flow is desired.

The sampling apparatus illustrated in FIG. 7 includes first attachment point 39 for introducing air into the sampling tubing. The air travels through a gas valve 40 to a filter 27 for sterilizing the air, then through check valve 38, where it captures a quantity of fluid from the perfusion loop and transports the fluid as a unitized sample through second attachment point 41, which may include a luer activated valve 42 as shown. The sampling apparatus is preferably automated or may be operated manually. In a preferred embodiment, samples may be diverted to a sample reservoir and maintained discretely with a fluid "spacer" (air or liquid) between samples. The fluid between samples may be an anti-fungal fluid. In another embodiment, the automated sampling system may flush the sample line before the sample is taken, the flush being diverted to the waste reservoir to insureg a fresh sample.

In another embodiment, the fluid may be automatically diverted through a length of tubing to the cartridge front or to an analyzer located outside the incubator. Samples may be diverted from the recirculating flowpath fluid or from fluid residing in direct contact with the cells and the fluidic loop flow may be reversed to improve homogeneity of the sample. Fluid may be automatically routed by a computer program, or a manual interface button. In another embodiment, fluid may be removed via a syringe from the manual sampling port.

In one embodiment of a biochamber, cells are grown in a space outside fibers carrying fluid through the biochamber. This space, which is sealed from the general fluid path other than across the fiber wall, is referred to as the extra-membranous or extra-cellular space (ECS). In another biochamber embodiment, cells are grown in suspension in the absence of fibers. Samples collected through sampling port 36 may include samples from the ECS of biochamber 10. Samples collected through sampling port 36 may include a suspension of cells. Samples may also include circulating fluid from various points in the perfusion loop. Samples may be collected via ultra filtration of the perfusion loop media through a membrane into the extra-membranous space and directed to the sample routing tube.

FIG. 7 also illustrates an attachment point 43 through which an injection into media reservoir 22 may be made, and an optional stir bar 44 within the media reservoir. Fluid may be automatically injected at intervals preprogrammed into the system. Programming may occur via a manual interface or via an external computer.

FIGS. 6 and 8 show alternative embodiments including alternate arrangements of several of the components illustrated in FIG. 7. FIG. 6 also includes an optional handle 45, a noninvasive LED sensor array 46 for, e.g., pH, glucose, or $O_2$ level detection and a display and control module 47, located on the cartridge outer shell. FIG. 6 further illustrates an optional cutaway 48 adjacent to the biochamber 10 for optical viewing or video monitoring of the operating biochamber. This configuration allows for visualization on a standard laboratory or other microscope, viewed from below with an additional light source available mounted on the cartridge, above the biochamber. An alternate embodiment allows the cartridge to be used with a modified docking station. The docking station may include a fixed CCD video camera that translates in and out along the y axis (depth of field). Alternatively, a CCD video camera may be mounted on an x-y-z translator that allows the camera to translate under each biochamber and then translate along the y (depth of field) axis for real-time visualization of the cultures. These images are sent to a computer or monitor that is located outside the incubator environment. In an alternative embodiment, this camera is outfitted to provide real-time fluorescent images when used in conjunction with fluorescent dyes, etc. and fluorescent light activation.

FIG. 8 includes an internal controller 49 with a user interface, a pH sensor 51, and an internal air pump 50 for integration with the sampling apparatus. In the illustrated embodiment, pH sensor 51 may be invasive or noninvasive. In one embodiment, pH sensor 51 is a pH probe.

Oxygenator 24 may be formed by coiling a length of gas permeable silicon or similar tubing. The oxygenator may alternately be a membrane positioned over a biochamber, valve, or another component of the flowpath. In an alternate embodiment, the oxygenator may be a hollow fiber membrane oxygenator. The oxygenator is preferably exposed to ambient air within the incubator during operation. The oxygenator brackets, if used, can be any mechanical, magnetic, or other device suitable for affixing a structure to the cartridge's outer shell.

The disposable portion of the pump, i.e., the pump tubing, may be made from silicon tubing or other biocompatible or compliant tubing which may include a one way check valve on either end. In one embodiment, it is an integral portion of the unitized disposable flow path and can be sterilized as such during manufacture of the flowpath. The pump may also include a lid for holding the pump tubing in place. Such a pump may operate by using a plate to squeeze the diaphragm and displace the fluid through one way check valves. The fluid displacement can be modulated and a varied pressure wave produced through variable electronic signals to the fluid displacement actuator. The pump itself may be affixed to the cartridge housing. The pump may be removable from the flowpath and housing for servicing or other purposes. In one embodiment, the pump is capable of providing a fluid flow rate of about 4 mL/min to about 40 mL/min. The pump is regulated by a feedback control process in concert with flow meters. The pump motor may include a direct drive with stepper or infinite position control. Position control can be modulated via computer control to create a variety of pressure head and pulse wave signatures including physiologic wave forms.

In an alternative embodiment, this pump is increased to a larger volume, multi-head pump. The pump head may be changed depending on the desired flowrate. The larger volume head allows the system to pump at 100-300 mL/min. The head design, in concert with a suitable valving configuration, may be used to generate, for example, a cardiac-signature pumping profile, with diastolic and systolic pressure. The larger flowrate pump may be used in concert with two high flow sensors placed within the fluid loop. These sensors allow for closed-loop feedback control of the pump to allow for precision flowrates. This higher flowrate is important for several cell types, especially for cardiovascular applications. An example is endothelial cells that typically line blood vessels. The endothelial cells require a high shear stress to organize appropriately in the lumen of the vessel. Another example of a cell type that requires hydrodynamic mechanical stresses is mesenchymnal cells that require such stimuli to generate a cohesive, robust extracellular matrix similar to those of native tissues. This embodiment may include a biochamber capable of housing a tubular tissue and applying controlled hydrodynamic training regimes to the tissue. In this embodiment, the tubular tissue may be based upon an acellularized tubular matrix with appropriate mechanical and biochemical properties to promote vascular tissue genesis.

Figure 14:
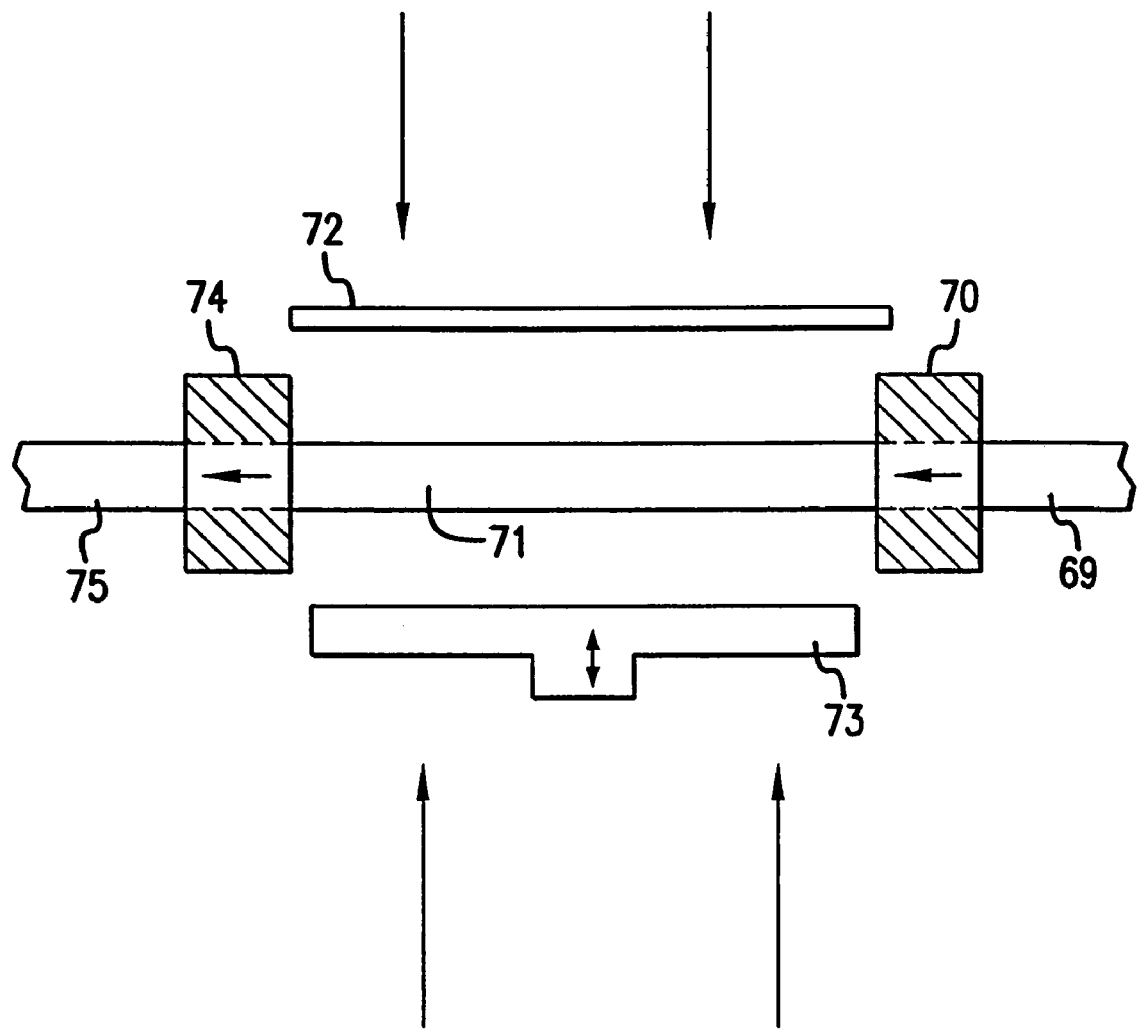
FIG. 14 depicts a pump and related structures in accordance with the present invention.

FIG. 14 illustrates one embodiment of a pump and related structures according to the invention. In FIG. 14, fluid flows through flowpath tubing 69 through a first one way flow valve 70 or check valve, into pump tubing 71. Pump actuator 73 compresses pump tubing 71 against pump lid or rigid backing 72, thereby forcing fluid from the pump tubing through a second one way flow valve 74 or check valve, into flowpath tubing 75. Flowpath tubing 69 and pump tubing 71 may be made of the same material or different materials. Another alternative embodiment of the pump is to allow for mechanical forces to be translated through the biochamber and directly to the cells and/or tissues. This is especially important for cells that are typically exposed to large levels of force in vivo and require such forces to maintain regular cellular and/or tissue function, like bone, tendon, ligament, cartilage, or muscle cells and/or tissues.

In one embodiment for mechanically stimulating the cells and/or tissues housed within the biochamber, the biochamber is fitted with an elastic or similar membrane that allows for deformation and force translation directly into the cell biochamber. This membrane interfaces with a cam or solenoid that is mounted underneath the biochamber, either on the cartridge or within the docking station. This cam interfaces directly with the membrane and deforms it to translate a force onto the cells. This technique also aids diffusion into three dimensional cell scaffolds that are placed as inserts into the biochamber and which can potentially impede flow through the normal flow direction In an alternate embodiment, a cam or lever is placed at the end of the biochamber instead of under it. The biochamber is mounted on the cartridge in such a way that the cam provides a rocking motion, ensuring even distribution of suspended cells within the biochamber. In an alternate embodiment, the mechanical stimulation is provided by a hydrodynamic pressure head. FIGS. 18A and 18B illustrate an alternate embodiment useful for mechanical stimulation of a tissue or cell specimen housed within the biochamber. In the illustrated embodiment, a linear actuator 94 is positioned below the biochamber. The linear actuator acts upon a lever arm 95 that passes through a flexible substrate 93 which is continuous with or embedded within the lower housing 97 of the biochamber. The lever arm 95 interacts with tissue structure 96 housed within the biochamber causing mechanical stimulation of the tissue specimen within the tissue structure. In the illustrated embodiment, media flows through the biochamber in the direction represented by arrows 98, but this direction may be reversed. In this embodiment, as illustrated in FIG. 18B, the fulcrum 99 of lever arm 95 is located within flexible substrate 93. In such a configuration, very small displacements within the flexible substrate caused by action (represented by double-headed arrow 106) from linear actuator 94 result in comparatively larger displacements within the biochamber.

Figure 19A:
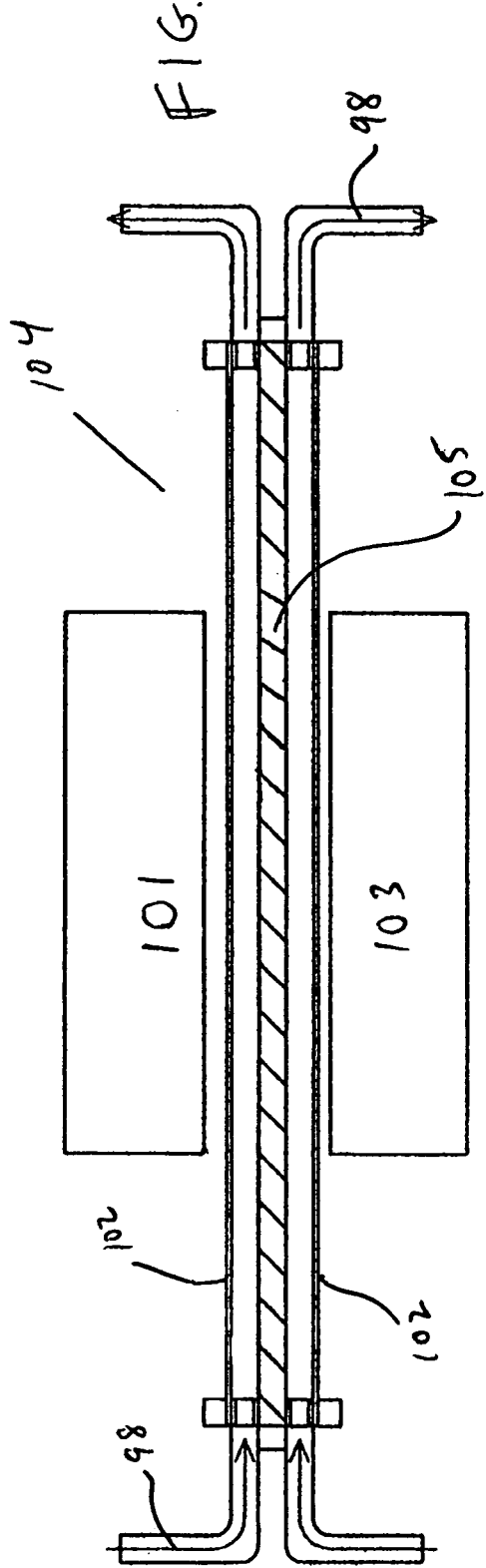
FIGS. 19A and B illustrate a biochamber providing compressive mechanical stimulation to a tissue specimen.
Figure 19B:
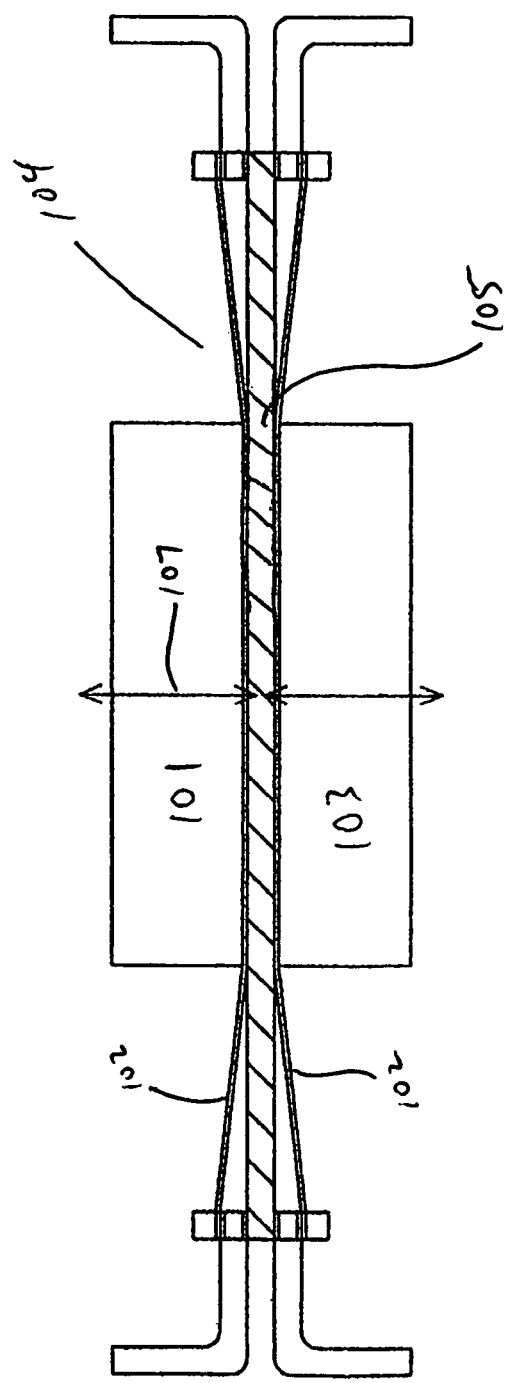

FIGS. 19A and 19B illustrate another alternate embodiment useful for mechanical stimulation of a tissue or cell specimen housed within the biochamber. FIG. 19A represents operation of the biochamber 104 in media flow mode and FIG. 19B represents operation in compression mechanical stimulation mode. The compression mode induces flow in the system with a check valve. The biochamber's interior space is defined by two compliant membranes 102. An actuator 101 is positioned above or below the biochamber 104 and a fixed surface 103 is positioned opposite the actuator, such that the biochamber 104 is positioned between the actuator 101 and the fixed surface 103. The movement of the actuator against the biochamber can provide compressive forces 107 to the cells and or tissues 105 housed within the biochamber, as illustrated in FIG. 19B by compressing the biochamber 104 against the fixed surface 103. The embodiment illustrated in FIGS. 19A and 19B is appropriate for compressive connective tissues, including meniscus found in load-bearing joints. In the illustrated embodiment, media flows through the biochamber in the direction represented by arrows 98, but this direction may be reversed.

Figure 15A:
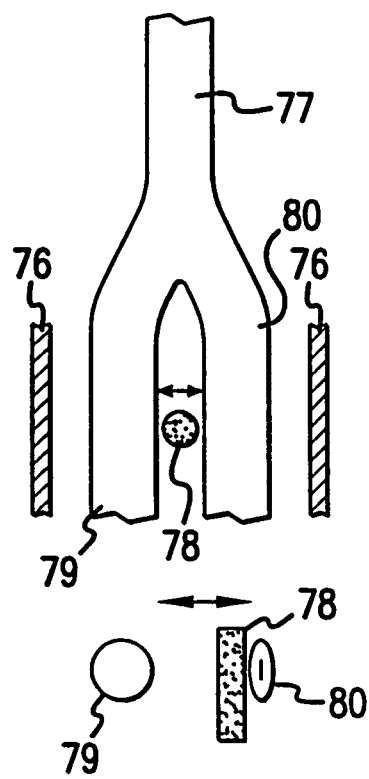
FIGS. 15A and 15B illustrate alternate embodiments of a valve for diverting media flow.
Figure 15B:
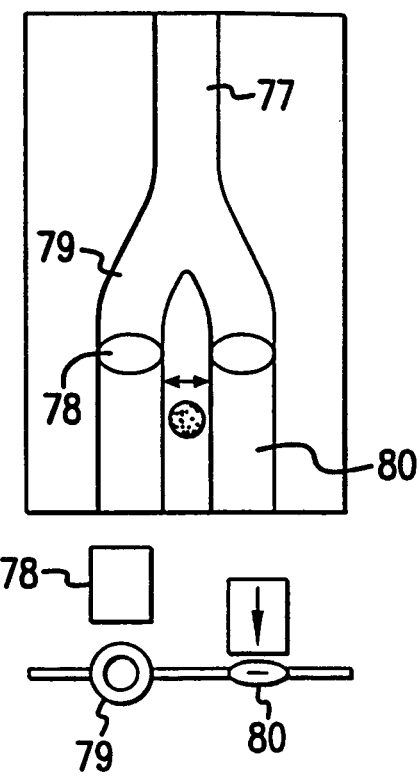

FIG. 15A illustrates an embodiment of a diverter valve suitable for use in the present invention. In the illustrated embodiment, fluid enters tubing 77 and is diverted to path 79 when actuator 78 occludes path 80 by compressing its tubing against a rigid surface 76. In FIG. 15B, fluid enters tubing 77 and is diverted to path 79 when actuator 78 occludes path 80 by compressing its tubing against surface 76. These figures provide a top view and a cross-sectional view of such valves.

The valve tubing may be flow path tubing routed through a slot in the valve. The valve tubing may be a diaphragm. The valve may be used as a diverter valve by running a flow path tube into a Y connector, then routing the two tubes through two slots on the valve. Such a mechanism only pinches one path at a time, thus allowing the user to select which path is active. Various valves and tubing or diaphragm structures may be selected by one of ordinary skill in the art given the teachings herein. The valve actuator is preferably capable of being held in position without external power. Suitable structures for attaching the unitized perfusion flow path components to the corresponding fixed structures of the cartridge housing include clips or any other fastener which sufficiently secures the path without impeding its operation.

Figure 20:
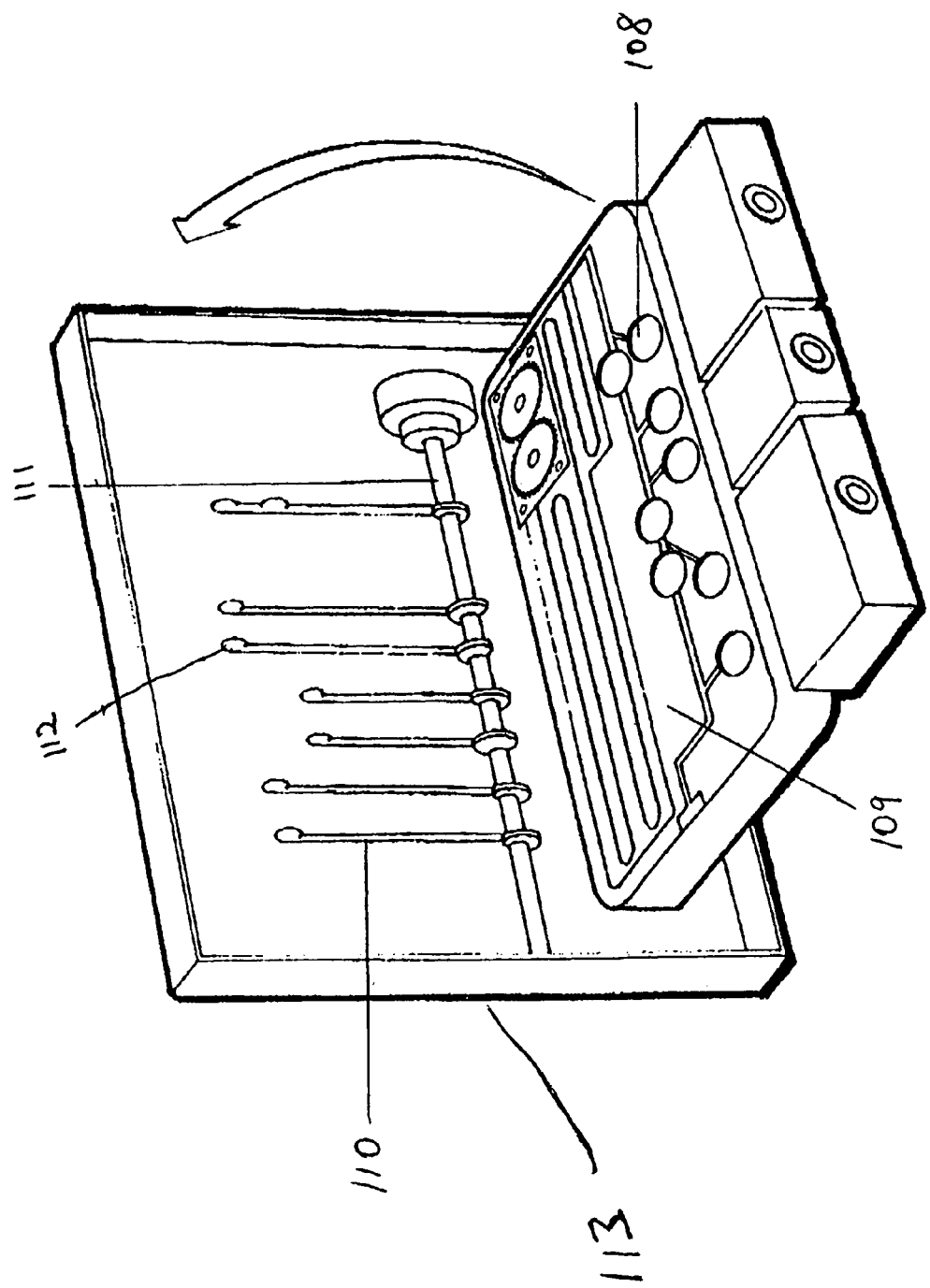
FIG. 20 illustrates an embodiment having an alternate valving configuration in accordance with the invention.

In an alternate embodiment, illustrated in FIG. 20, the valves 108 are located on a disposable flow-path 109 and are actuated by lifters 110 located within the non-disposable cartridge 113. The lifters may include valve actuators 112 which contact the valves to occlude the flowpath and divert flow. The lifters may be controlled by a cam-shaft 111 that is rotated to control the position of the lifters, and thus the open/closed state of the valves. The disposable flow path integrates with the cartridge by swinging into place similar to the manner in which an audio cassette swings into place in a front-loading audio cassette player. In this way the flow path and thereby the valves are precisely aligned with the valve actuators on the cam-shaft lifters. This design allows for precise fluid routing in a mechanically robust system that is amenable to a multitude of different fluid flowpath arrangements depending upon the position of the cam shaft, which is computer-controlled and based upon the user's input.

In alternative embodiments, one or more noninvasive sensors are spectroscopy sensor arrays containing a group of LED emitters and detectors oriented such that absorption of light through the media can be examined. Such a sensor can detect frequency spectrum of the media, and provide, for example, pH level, glucose content, or $O_2$ content determinations using NIR wavelengths. The sensor can be mounted to the cartridge. In a preferred embodiment, the flow cell is a transparent tube. In another embodiment, the flow cell is positioned in a groove within a block or other body affixed to the inner surface of the cartridge outer shell. In an alternate embodiment, the sensor and flow cell are incorporated into a single unit.

The media and waste reservoirs may have a capacity of about 100 mL to about 500 mL each. However, any other size can be used and the cell culture system of the present invention can accommodate reservoirs of various fluid capacities, either within the incubator or in large volume carboys placed outside the incubator (for volumes larger than 500 ml). Fluid volumes may be selected to accommodate a variety of different cell types. Some cell types have metabolic needs in which fluid volume greater than 150 mL is preferable. Some experimental protocols suitable for use with the present invention use small volume injection of a test compound, which can be provided from a reservoir within the cartridge or injected by various other means as discussed herein. The reservoirs may include a sealable, removable lid to allow fluid to be placed into the reservoir. The lid may also include a drop tube for drawing media or other material from the reservoir and a filtered vent of about 0.2-micron or other suitable porosity to maintain sterility. The reservoirs may be made of autoclavable plastic or glass, or any suitable substance for use in holding fluid in accordance with the present invention. The vented lid is preferably made of sterilizable plastic.

Any sterile biocompatible tubing is suitable for use in the present invention. Tubing is preferably silicone. Tubing may also be a commercially available tubing such as Pharmed, Viton, Teflon, or Eagle Elastomer. In one embodiment the tubing has an inside diameter of about 3/32" and an outside diameter of about 5/32"; however, any other suitable dimensions may be used. Such tubing may be utilized for, e.g., diaphragms, or tubing in connection with valves, the oxygenator, and between components of the perfusion loop. Tubing diameters may be used to control pressure heads since flow rate through the system may be determined by the pressure head and the point of greatest resistance to flow in the system. In an alternate embodiment, this concept is used to advantage to limit the flow or maximize the flow to a specific section of the flowpath. In an alternative embodiment, the tubing diameter and length is minimized to minimize the total residual volume in the tubing and to maximize the effect of diluted substances in the media, such as pharmaceuticals or growth factors.

Efficient collection of the tissue or cells at the completion of the culture process is an important feature of an effective cell culture system. One approach is to culture cells in a defined space without unnecessary physical barriers to recovery, so that simple elution of product results in a manageable, concentrated volume of cells amenable to final washing in a commercial, closed system or any suitable cell washer designed for the purpose. An ideal system would allow for the efficient and complete removal of all cells produced, including both adherent and non-adherent cells. Thus, various different biochambers can be used in accordance with the present invention. As used herein, a biochamber includes any bioreactor suitable for use in accordance with the invention and can include any such device for growing, maintaining, transfecting, or expanding cells or tissues. The biochamber may be, for example, a hollow fiber biochamber or bioreactor having luer fittings for attachment to the flowpath. Various biochambers and bioreactors are adaptable for use with the media flowpath assembly cartridge of the present invention given the teachings herein.

Figure 9:
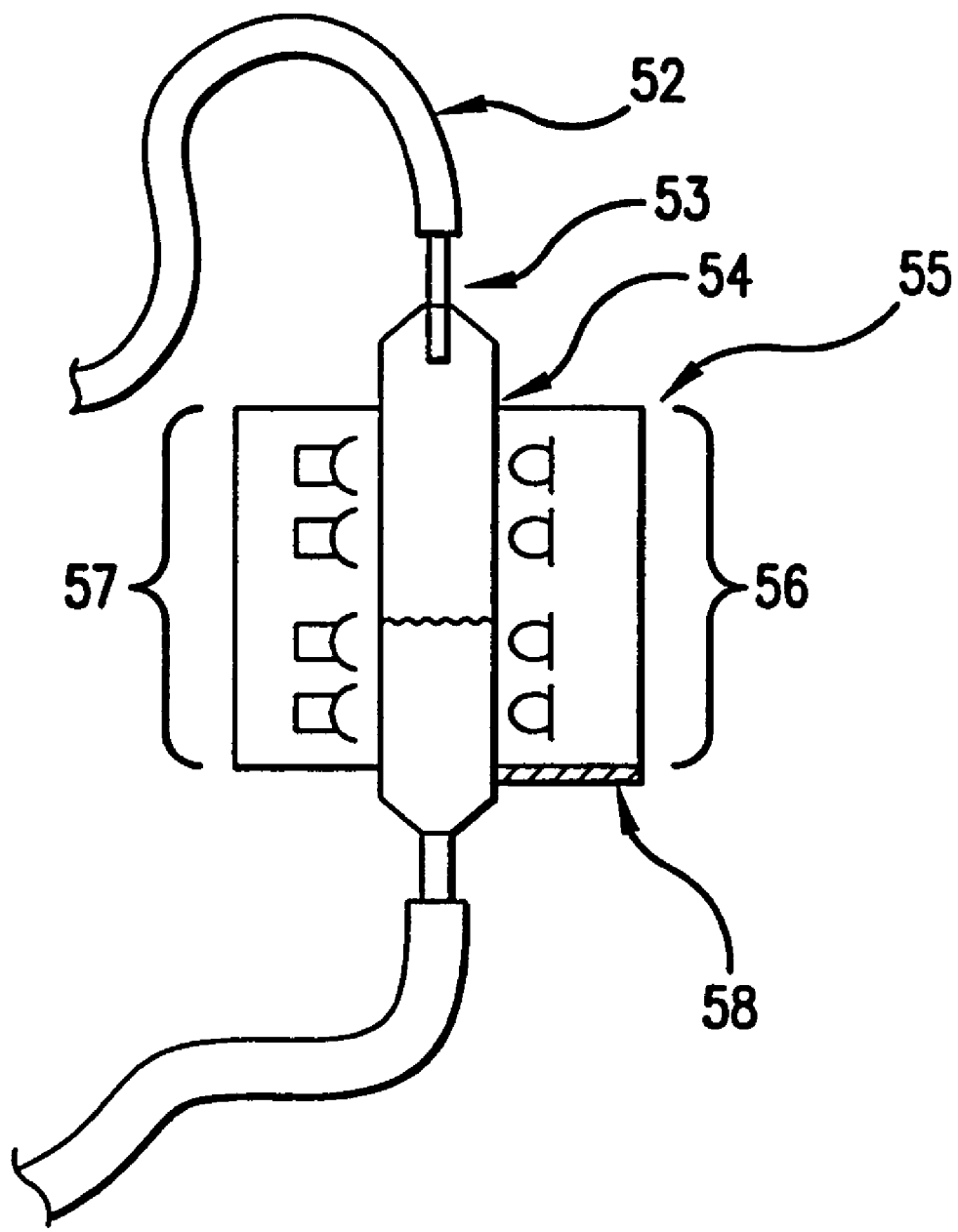
FIG. 9 depicts a drip chamber and noninvasive sensor in accordance with the invention.
Figure 10A:
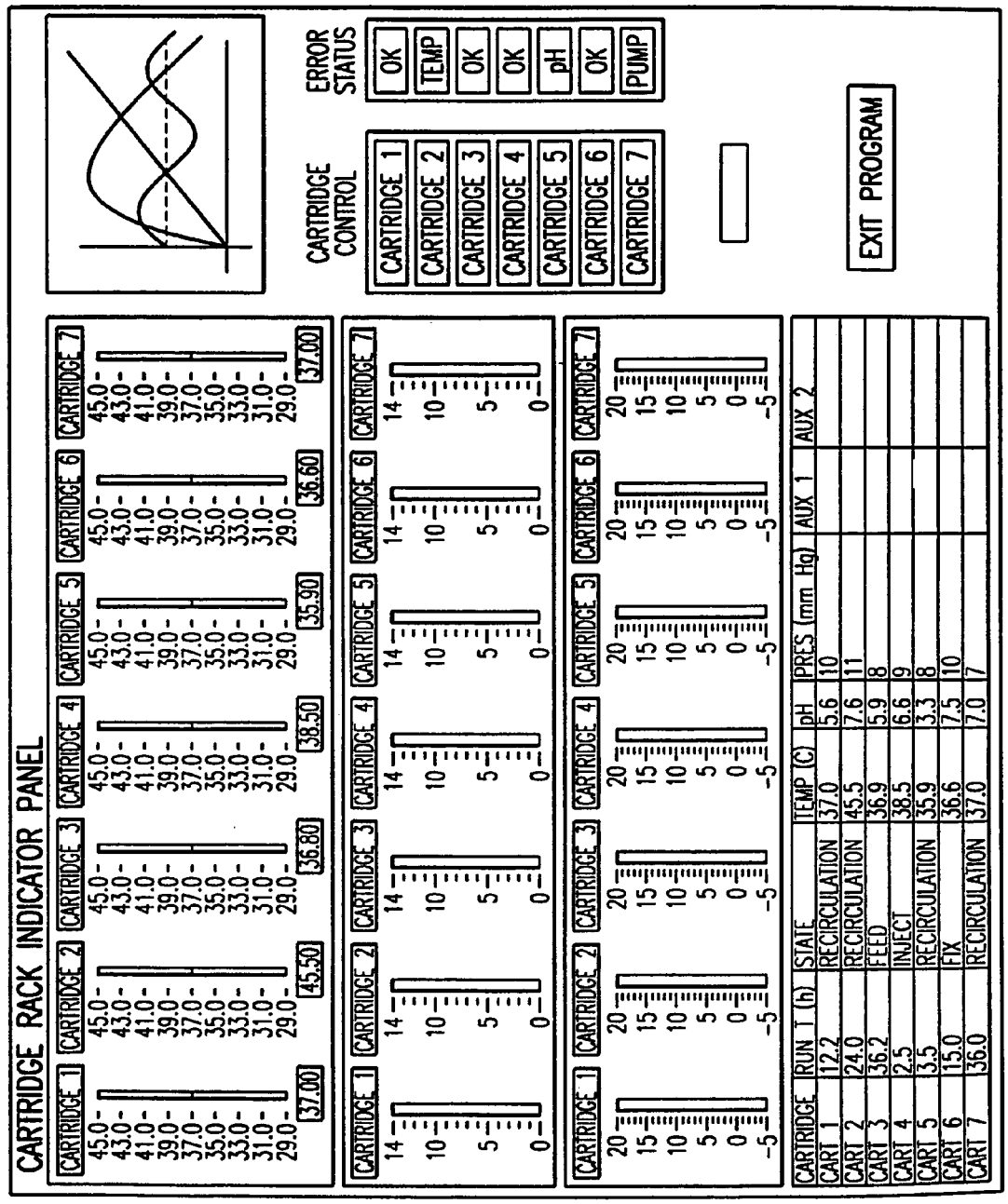
FIG. 10A shows an external cartridge controller interface.
Figure 10B:
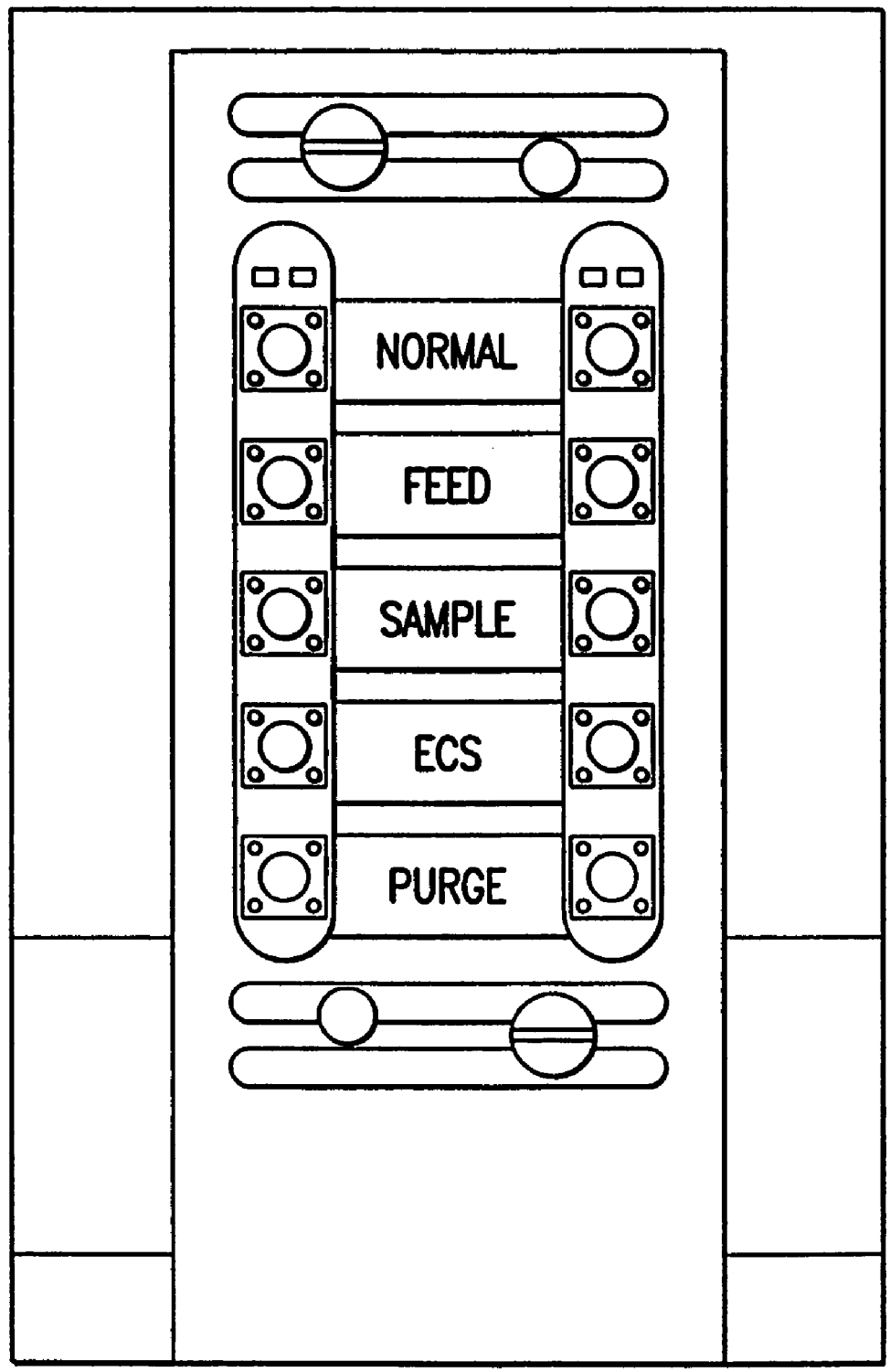
FIG. 10B shows a manual interface located on an individual cartridge.

FIG. 9 depicts one embodiment of a drip chamber and noninvasive sensor for use in the sterile media perfusion loop. During use, fluid flows through feed tube 52 and is released in discrete droplets through drip aperture 53 into partially filled, preferably transparent flow chamber 54 before exiting through tubing at the bottom of the drip chamber. As the droplets fall from the aperture, they pass through a noninvasive sensor which includes housing 55 having an emitter element or array 56, a photodetector element or array 57, and a computational chip 58. The emitter array and photodetector count the droplets and, with the computational chip, determine droplet frequency to calculate a flow rate or a volume of fluid passing during an event. The drip chamber may be positioned between the pump and the oxygenator (which precedes the cell biochamber) or located at various positions within the perfusion loop. A preferable location is downstream from the cell biochamber. Another preferred location is upstream from the pump. The sensor may be linked to a pump for providing precise injection of fluids to the recirculating media stream. Injected fluids may include media, drugs, or other additives.

A particularly preferred biochamber is a biochamber convertible for use in static cell culture or in a cell perfusion apparatus and includes a first chamber, a cover, a seal rendering the first chamber removably connectable to the disposable cover, and at least one insert positioned between the first chamber and the disposable cover, thereby forming a second chamber. The preferred biochamber operates in two modes, open or closed. In the presealed phase or mode, the biochamber acts as a petri dish and allows for manual cell seeding and growth prior to sealing the biochamber and attachment to a flow system. In a preferred embodiment, the biochamber has a lip that acts as a sterile barrier which allows for gas diffusion but keeps bacteria out of the cell space. Cells can be grown in the extra-membranous space, which is sealed from the general fluid path other than across the membrane wall. Once sealed, the biochamber can be seeded with cells above and below the membrane insert. Ports may also be used to collect extra membranous samples throughout an ongoing experiment. In preferred embodiments, the biochamber remains horizontal in orientation and cell retrieval is carried out manually.

Figure 11:
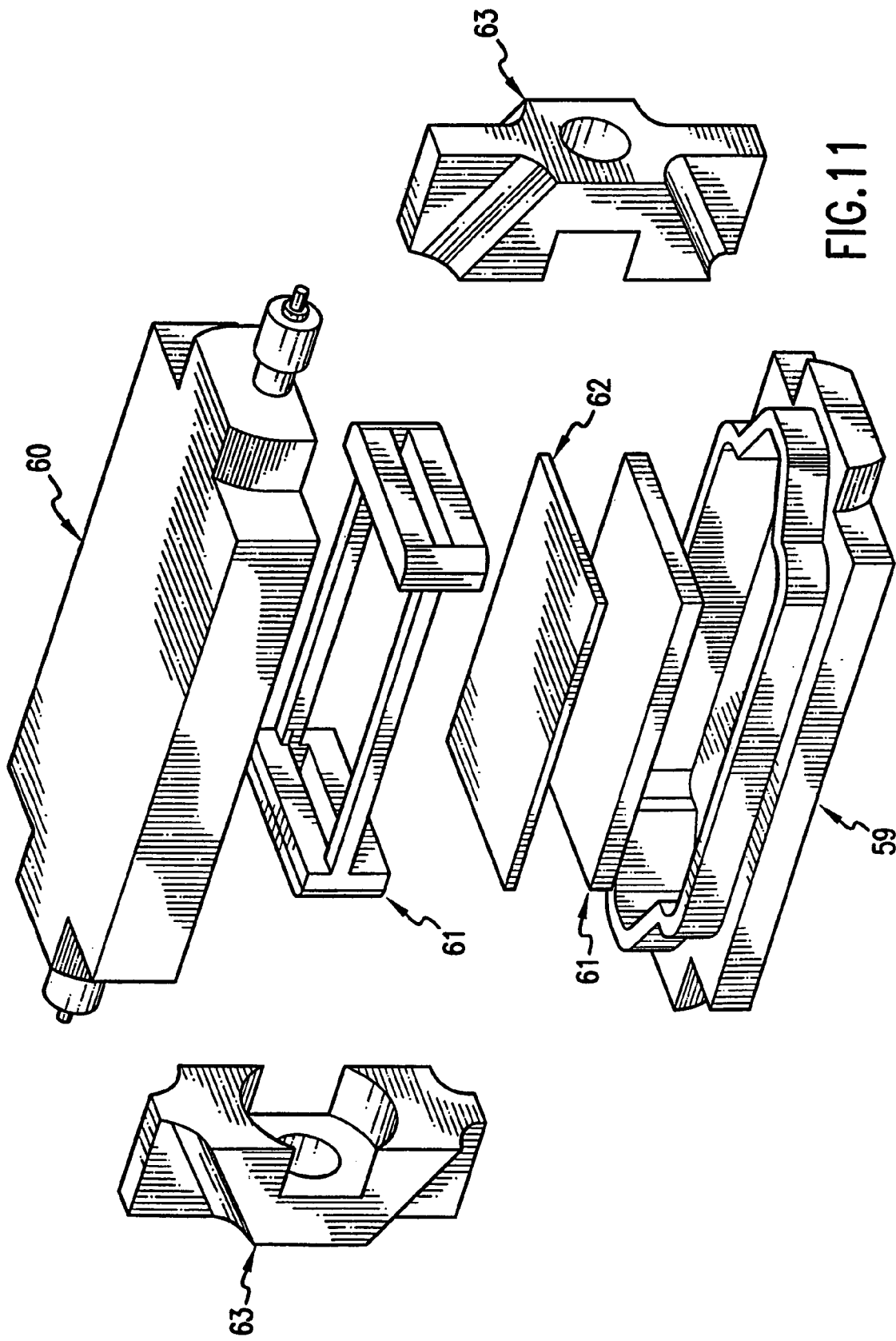
FIG. 11 shows an exploded view of a biochamber in accordance with the invention.

Referring now to FIG. 11, the illustrated biochamber embodiment includes a bottom chamber 59, a cover 60, a brace 61 for holding at least one insert 62 between the bottom chamber 59 and the cover 60. The biochamber preferably includes diffusers on each end 63 for modifying pressure characteristics of incoming fluid to provide an evenly distributed flow. FIG. 12 shows components of an alternate embodiment of a biochamber according to the invention, including cover 60, braces 61, and insert 62 between two braces 61. A membrane insert is shown 62. The biochamber may accommodate a variety of selectable barrier inserts, such as hollow fibers and membranes, for cell growth. Inserts suitable for use in the present invention include semipermeable membranes. Additional inserts suitable for use in the present invention include optically reflective surfaces for enhanced contrast video microscope observation, and a variety of three-dimensional growth matrixes such as gels, elastin conduits, bioabsorbable materials, and scaffolds for improved growth and cell orientation. The biochamber can also accommodate inserts and diffusion patterns that allow active laminar flow and passive flow techniques. Inserts are preferably from about 0.001 inch to 0.1 inch thick. A grooved shelf may be provided to align the membrane assembly and provide structural support. FIG. 12 also includes connections 64 for flowpath tubing from the biochamber to the perfusion loop.

Figure 17:
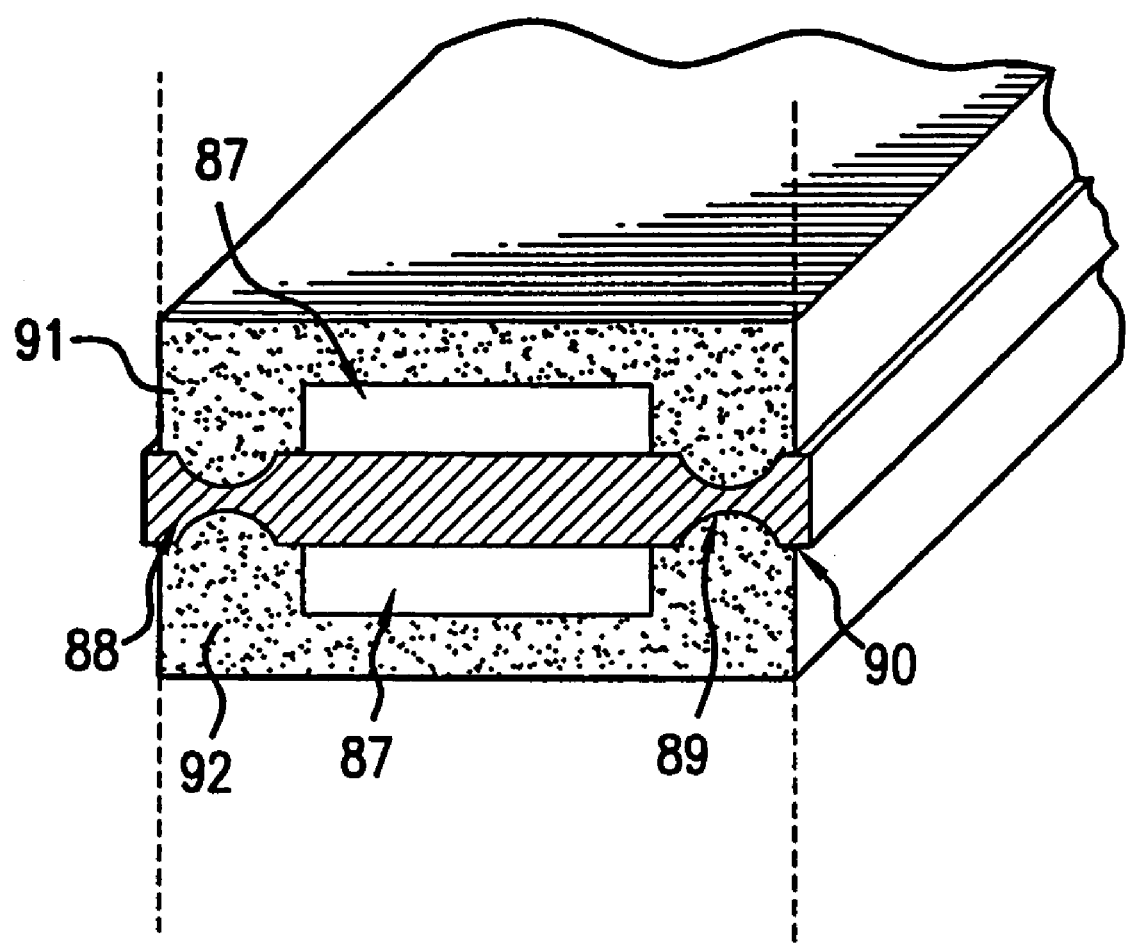
FIG. 17 illustrates a biochamber dual o-ring and air gap seal.

Referring to FIG. 17, in one embodiment a biochamber includes a seal utilizing a gasket with dual sealing interfaces and an integral air gap to prevent contamination of the biochamber. The biochamber and o-ring sealing surfaces form an environmental seal 88, an air gap 87, and a fluid seal 89. The combination seal and air gap ensures that environmental contaminants cannot come into contact with the fluid gasket seal 90. Fluid o-ring seal 90 can provide microscopic fluid interface channels, which might otherwise be transversed by biologic contaminants such as viruses, mycobacterium, and bacteria. The gasket air gap is formed when the two halves 91 and 92 of the biochamber are mated and air, which has been HEPA filtered or made sterile through any suitable method, is trapped between the two gasket interfaces. The environmental seal 88 prevents contaminants from reaching the air gap 87, which provides an area void of fluids and fluid micro channels which, if present could permit contamination or breaching of the fluid seal 90. The sealing o-ring and biochamber halves preferably form a continuous color change to signal the appropriate mating and seating of the sealing surfaces.

In alternate embodiments, the cover and base may have a color verifiable sealing surface that is established and maintained via threaded twist end caps or pressure maintenance solution. Such a sealing surface may reveal one color when the cover and base are sealed and a different color when the seal is broken. The sealing surface can include ridges for securing mid chamber inserts, the seal and inserts preferably being reversible and removable. In particularly preferred embodiments, multiple chamber ports allow access and flow to the central media chamber and to medium and cell products captive on either side of the insert barrier. The chamber ports also preferably provide fluid interfaces for automated perfusion manipulations such as sampling and injections. In an alternative embodiment, the sealing method may include a modified tongue and groove interface fabricated from compliant materials to lock into the groove such that the internal pressure on the seal reinforces the tongue and groove. The two surfaces may then seal in much the same manner as do those of a Tupperware™ container or Zip-Loc™ bag. More than one groove may be employed to provide for trapped air, to prevent ambient air from reaching the liquid seal interface.

Figure 13A:
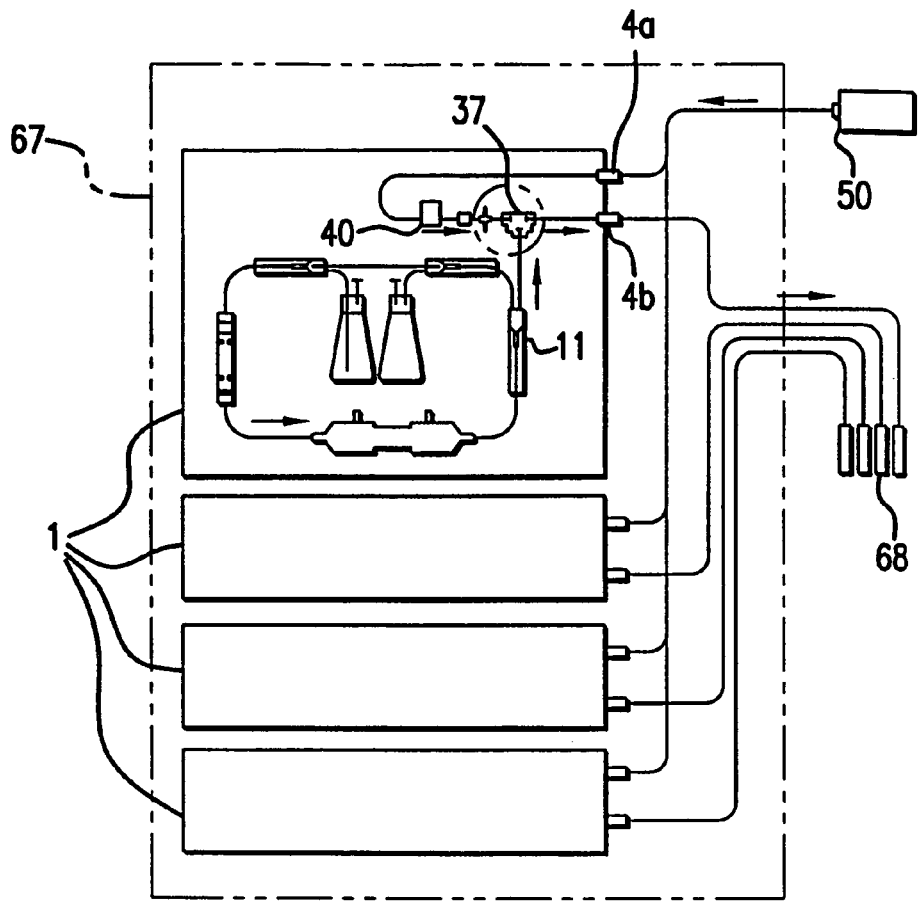
FIGS. 13A and B are schematics illustrating an automated sampling apparatus connected to a flowpath assembly cartridge perfusion loop in accordance with the invention.
Figure 13B:
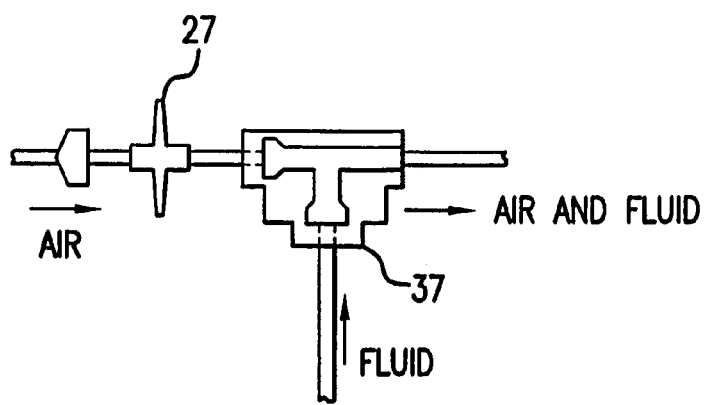

FIG. 13 is a schematic diagram of one embodiment of an automated sampling apparatus according to the present invention. The illustrated embodiment shows the sampling apparatus having an air pump 50 connected to a plurality of flowpath assembly cartridges, 1, housed within an incubator 67. Alternatively, each cartridge can have its own air pump. A sample is collected by first diverting a sample from the flowpath using a diverter valve 11. The diverter valve may be a pinch valve. The sample travels to a one way or check valve 37. Valve 40 (optional, for use with another routing or carrier fluid source; otherwise air pump 50 is used) is then opened. Air from air pump 50 passes through sterilizing filter 27 and through check valve 37, thus capturing the sample and forcing it to a collection receptacle 68. The sterilizing filter may be, for example, a 0.1 or 0.2 micron filter or a series of filters, or any other method or structure suitable to render the routing air or other carrier fluid free of biologic contaminants. The valve 40 is only required if the routing fluid is other than incubator air. A single air pump can be used with an external air source and manifold off of the air source to a plurality of cartridges. The preferred approach, however, is for each cartridge to contain the necessary hardware to perform its own sampling. The sampling apparatus may be automatically operated by pressing a button located on the cartridge. The button preferably is marked to indicate that it is for sampling. The button may be located on the front of the cartridge. In another embodiment, the sampling apparatus is operated through programmed control by an external computer. The sample may be diverted to a collection container. In one embodiment, the collection container is a tube. In another embodiment, the collection container is positioned on the front of the cartridge. The sample tubing may be flushed into the waste stream before the sample is collected for ensuring a fresh sample. In an alternate embodiment, the sample may be diverted to a sample reservoir located on a stepper motor for collection of multiple samples without operator intervention. Each sample may remain in a sample reservoir until collected for analysis, allowing for sample collection during periods of time when an operator is unavailable. In a preferred embodiment, each sample collection reservoir may be connected by a resterilizable connector where a resterilization technique, such as the application of heat or steam, is applied to the connector to resterilize the interface after the sample has been retrieved.

The automated sampling apparatus eliminates potential breaches of the sterile barrier and thus minimizes the risk of contamination without the use of bactericides or fungicides, which may interfere with the integrity of the sample. Potential problems associated with traditional sterile barrier culture manipulations and perturbations, such as removal of the cultures from their temperature and gas environment to room temperature and room air for processing under a sterile hood facility, are eliminated. A computer controlled sterile air pump allows integration with analysis instruments that require fixed timing by controlling sample duration and pump speed. Residual medium may be removed via a purge cycle of the collection device. In-line residual may be minimized at the point of sterile media or cell diverter and through the use of hydrophobic routing materials and surface modification. Use of periodic sterile air purge through the sample routing tube can be utilized to prevent aerosols and endotoxins from migrating back through the sample routing tube. The routing tube end when not interfaced with the collection device is preferably maintained in an anti-microbial bath. The apparatus provides a small sample (typically 0.5 to 5 mL), which is extracted from the flow path or extra-membranous space of the cell biochamber and routed via a bubble of sterilized air within the collection tube to the final collection point. For certain samples and applications any suitable alternative fluid carrier, liquid or gas, may be used to allow transport of the sample within the system and to a collection receptacle or analysis instrument.

In addition to automated sampling, the invention also permits manual cell or tissue harvest, and manual cell seeding and manipulation, under a sterile hood, with manual dual port syringe flush cell seeding. In one embodiment, a manual access port is provided for injection of cells. Injection may occur through the manual access port via a syringe or needle.

In terms of growth condition optimization and process control, the present invention provides for continuous set point maintenance of various cell culture growth parameters through sensor monitoring and feedback control of pump, valves, and other equipment suitable for a given cell culture or tissue engineering application. Data, pertaining to, for example, pH, temperature, flow rate, pump pressure, waveform, and oxygen saturation can be displayed and stored. The incubator is typically separately controllable for temperature and gas conditions. System program and status parameters, such as media flow and flow dynamics through low drip flow chamber, inline pressure sensor(s), and pump motor control, can be controlled via a computer interface allowing operator control on a PC or control pod directly or allowing protected remote communication and program modification via a modem or internet connection. Sampling increments and drug dosing can also be preprogrammed or entered directly on a separate computer or can be entered via a control pod touch pad or other interface located on the docking station or in each cartridge.

The computer interface preferably provides a display for real-time or logged data of parameters from each cartridge including, for example, temperature, pH, flow rate, pump pulse waveform, and various scheduled events, including, for example, injection of fresh media and other fluids, and automated sampling. The pH, flow rate, pump pulse waveform, and other parameters are preferably feedback regulated from a set point selected and entered by the operator. Temperature is preferably regulated by the incubative environment. In one embodiment, the cartridge logs data without need for a separate computer. In another embodiment, a cartridge may include an unique digital identification when connected to the rack, for the purpose of identifying the particular experiment being run in the particular cartridge or the status of the experiment upon disconnection. Each cartridge may be keyed to a particular rack slot once operation begins, which prevents its continued operation if disconnected and replaced into an incorrect or different slot. Alternatively, each cartridge may operate independent of rack slot location via the cartridge's unique digital identifier. Each cartridge preferably includes a manual interface which includes LED's to indicate the cartridge's state of operation, and which provides the operator an interface for entering set points. The interfaces also may operate while the cartridge is not in the rack.

Each cartridge preferably includes a local controller such that each noninvasive sensor generates and transmits information in the form of an electrical signal to the local controller. The signal may be transmitted by an electrical connection either directly to the local controller or first to an amplifier or transmitter and then to the controller via a communication path or bus. The communication may be transmitted serially or in parallel.

Figure 16:
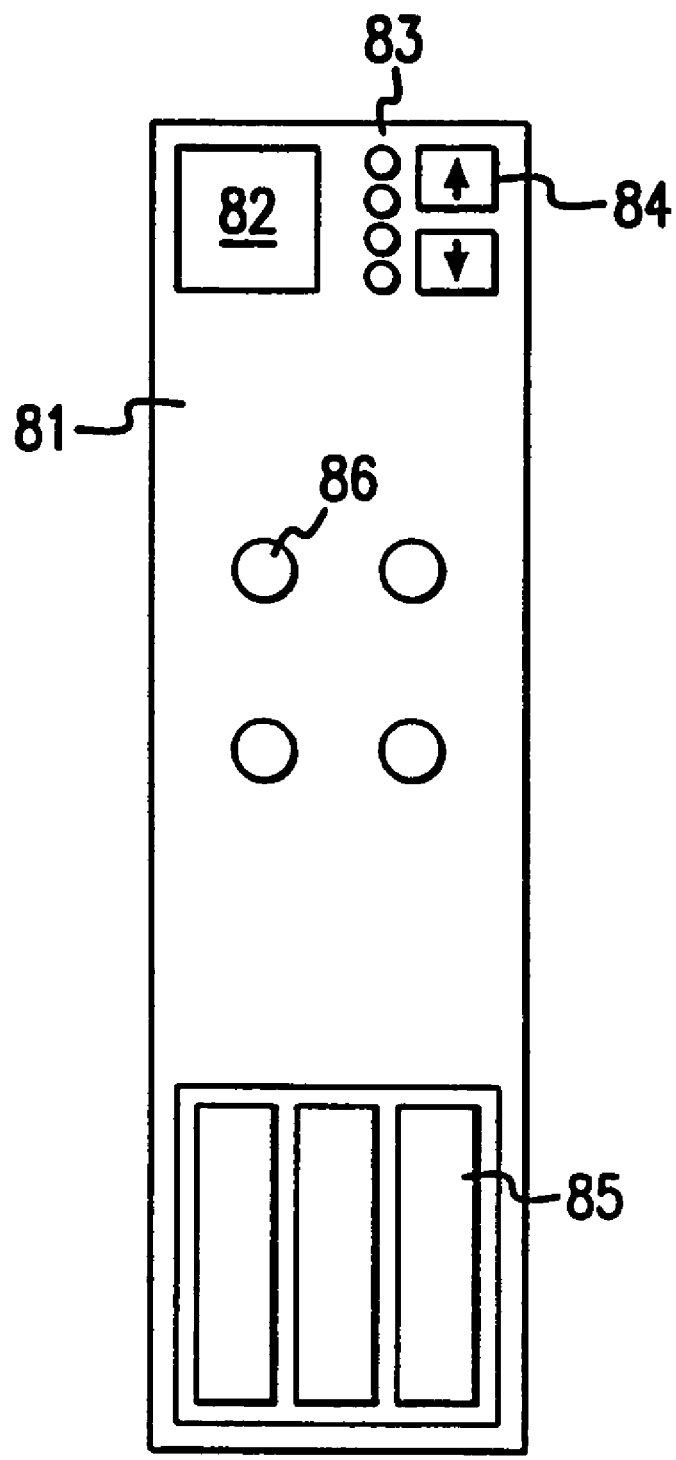
FIG. 16 illustrates the front face of a cartridge embodiment.

FIG. 16 shows one embodiment of the front face of a cartridge 81 of the present invention, including a display 82, LEDs 83, operator interface 84, sample collection tubes 85, and sites 86 for injection or sampling.

The controller includes information corresponding to a measured value with a set point which is either preprogrammed within it (such as in a chip) or can be entered using a touch pad or interface located on the cartridge or as part of a PC or other central computer system connected to the local controller. When the controller receives the signal from the sensor, it determines whether to move the process value closer to the programmed set point (i.e., change the flow rate, divert media flow, etc.) and transmits the information to the pump, altering its flow rate if necessary, or to the valve, diverting media flow if necessary or desired. This feedback control is preferably continuous throughout operation of the system. Automatic warning alarms may be utilized to alert the operator via, for example, telephone or internet connection and are preferably audible.

The local controller may be connected by a communication path to the connector located on the cartridge which in turn is connected to the connector located on the rack when the cartridge is docked. The rack can then be connected via a communication path to a central computer or controller. The communication path connected from the rack to the central computer can transmit separate information from each of a plurality of cartridges docked in the rack to the central computer. The central computer can also transmit information to each cartridge or all cartridges via a communication path from the computer to the rack and the rack to each individual cartridge. The central computer can also store and analyze information received from the cartridges.

Growth condition optimization is preferably achieved through noninvasive monitoring and precision control of numerous parameters, including flow rate, physiologic pressure and pulse wave, media addition, oxygenation and pH. In addition, sampling, fresh media addition, and drug dosing, etc., can be automated by programming a valve to divert media flow at a desired time or in accordance with a desired schedule. The process control parameters can be modified as desired to provide additional features, such as drug injection and biological function monitoring, to achieve the desired optimal results in various research and clinical contexts depending on the particular end use application.

Consistent with this growth condition optimization, each cartridge can provide a separate experiment in which any combination of configurations and events in a timed or threshold triggered fashion can be maintained, including, for example, medium recirculation at a specified flow rate, pressure wave and shear. Once programmed, each cartridge can be operated with only a power source, such as through the attachment of a power cable or with an on board battery pack, to facilitate individual cartridge processing, analyses, or manipulation under sterile laminar flow hoods or various external analytical devices.

The cell culture system can operate in several modes. A recirculation mode keeps the media flowing through the closed perfusion loop. Alternatively, a feed/sump mode can be used in which valves divert the flowpath to supply fresh media from the media reservoir and drain waste from the perfusion loop to the waste reservoir. Switching modes may be achieved, for example, by preprogramming a predetermined volume of fresh media to be injected at predetermined intervals. Switching modes may also be achieved through the feedback control loop connected to the pH sensor. For example, the operator may input into the computer a desired pH set point. When the pH sensor detects a pH level below the set point, the system automatically injects a predetermined volume of media into the recirculating flowpath. The pH is then continually monitored and fresh media again injected as needed.

Drugs or other substances can be injected into the perfusion loop or into the biochamber for testing their effects on the growing cells and tissues. The invention further provides for automated injection of drugs or other substances directly into the media reservoir or the fluidic path leading to the desired area. Alternatively, manual injections can be performed by using a syringe and a septum attached to the media reservoir or through the manual injection site on the cartridge front face. Such manual injections may be performed with the cartridge remaining in the incubator, or at another suitable location, such as, for example, under a sterile hood during cartridge processing. Alternatively, drop by drop additions may be added and allowed to enter the media reservoir or fluidics stream.

Numerous end use applications can be achieved with the apparatus of the present invention. Numerous kinds of cells, including anchorage dependent and non anchorage dependent cells (i.e., those capable of growth in suspension) and various tissues can be grown, harvested, inoculated, and monitored through use of the present invention. More complex cell models may be achieved by using various inserts in the biochamber or through optimization of growth parameters. The system may also be used in numerous genetic and metabolic engineering applications.

Samples of fluid circulating in the loop can be extracted, as can cells or tissues growing or being maintained in the biochamber. Cells can be used in the apparatus to produce a final product of interest, such as through hybridoma production of monoclonal antibodies or other products, or cells themselves can be cultured as the final product.

When a plurality of flowpaths are in operation together in a rack, the system permits parallel optimization and scale up. An operator can make one or more adjustments to one of the flowpath loops, and quickly obtain information and assess its impact on the cells or tissues being cultured. The apparatus also permits high through put and quality assurance by providing the ability to conduct parallel experiments or processes under identical conditions. Multiple racks may also be removably connected and operated together for multiple experiments or to scale up cell production. The present invention also permits optimization of, for example, any or all of the following: cell selection, growth and viability, cell growth conditions, cell metabolism or bioproduct production, development of medium for a particular cell type for limited cell populations, processing of metabolic products, and expansion to several cell products and cell co-cultivation.

Tissue engineering of small diameter vascular graphs (SDVG) is one example of the numerous processes which can be advantageously conducted within automated bioculture and bioculture experiment systems according to the present invention. SDVG's are intended as a vascular replacement therapy for patients with cardiovascular disease in need of vessel replacement for small (<6 mm) vessels. Cardiovascular disease is the leading cause of morbidity and mortality in the developed world, and artificial replacement therapies for SDVGs currently have 40% thrombosis rates after 6 months. Treatment by replacement with autologous grafts is not ideal in that it does not address those patients without appropriate tissues for grafting and leaves a functional vascular deficit at the donor site. The ideal replacement leaves no functional deficit in the individual, withstands the immediate mechanical demands of the implant sight, does not promote thrombogenesis, and can adapt to long-term requirements of the tissue. To be commercially and clinically feasible, xenosourced and/or minimally-invasively harvested autosourced cells or materials should be used. Previous attempts have used immunogenic xenografts, neonatal allogeneic cell sources, or have not been mechanically sufficient.

Systems according to the invention using precision automated feed back control can mimic the in vivo developmental environment for optimal tissue development. In addition, systems according to the invention provide biocompatible materials and physiological requirements for cells to maintain viability, proliferate, differentiate and organize into SDVGs and various complex tissue structures depending on the cells used, selection of biochamber, perfusion conditions, and media and other factors.

An improved SDVG product and method according to the present invention utilizes an acellularized conduit (e.g., non-immunogenic elastin) to provide a natural substrate with appropriate geometry and compliance. The conduit is placed in a biochamber according to the invention and seeded with autologous cells that can be harvested by minimally-invasive outpatient biopsies. An automated bioculture system according to the invention reproduces the dynamic in vivo environment and thus mechanically "trains" the seeded conduit in the presence of media additives that promote the development of tissue comprised of differentiated cells and extracellular matrix (ECM) capable of withstanding the mechanical loads placed on the tissue in vivo. The vessels, once they have achieved appropriate mechanical properties, are then seeded with liposuction or similarly non-invasevely harvested autologous vascular endothelial cells (VEC) and trained in the perfusion system of the invention prior to surgical implantation.

More specifically, in this embodiment an SDVG is manufactured, preferably utilizing a large volume, multi-head pump, in concert with a valving configuration to generate a cardiac signature pumping profile with diastolic and systolic pressures. The high flow rate pump, together with a biochamber capable of housing a tubular tissue conduit, is utilized to apply high shear stress and controlled hydrodynamic training of the tissue within the perfusion loop. The SDVG manufacture process utilizes as a tissue scaffold starting material a xenogeneic or synthetic conduit (potentially elastin) with appropriate dimensions. The conduit is seeded with appropriate cells, for example, (of autologous or heterologous source) fibroblasts (potentially from punch skin biopsy), smooth muscle cells potentially from carotid artery biopsy), and myofibroblasts. The seeding may use orbital shaking or any suitable method, if desired, to enhance cell adhesion. The cells are then allowed to remodel the conduit while being perfused in the bioreactor and monitored through automated sampling, video microscopy, etc. During this stage (from a few weeks to several months in duration) the cells differentiate and develop an organized ECM and form with the ECM a coherent tissue. Media may be supplemental with various factors, including, for example, one or more of the following, to promote production of ECM: ascorbic acid, copper ion, and amino acids. Growth and differentiation optimization are readily achieved using automated feed back controlled monitoring and precision adjustment of flow rate, physiological pressure and pulse wave, media addition, oxygenation and pH.

VECs (from, e.g., autologous liposuction harvest) are then introduced to the ECM, and perfusion is continued for about 2-7 days or other time period sufficient to produce a functional SDVG. Such hydrodynamic training available in the invention causes the VECs to differentiate, form a functional neo-endothelium. The resulting tissue engineered product, now rendered non-thrombogenic my virtue of the neo-endothelium, is then removed from the biochamber and surgically implanted to a patient in need of an SDVG.

The above description and examples are only illustrative of preferred embodiments which achieve the features and advantages of the present invention, and it is not intended that the present invention be limited thereto.

What is claimed as new and desired to be protected by Letters Patent:

1. A culture apparatus for use within an incubator, said apparatus comprising:
    a rack for supporting at least one flowpath assembly cartridge; and
    at least one media flowpath assembly cartridge, said cartridge including:
        a housing;
        a control interface;
        a non-invasive sensor; and
        a sterile media perfusion flowpath loop removable from said housing without breaching flowpath sterility, said media perfusion loop comprising:
            a pump;
            at least one valve adapted to prevent or divert media flow;
            at least one biochamber in fluid communication with the pump and the at least one valve;
            a gas permeable membrane in fluid communication with the pump and the at least one valve;
            a media reservoir in fluid communication with the pump and the at least one valve; and
            a flow cell removably positionable within said non-invasive sensor.

2. A culture apparatus for use within an incubator, said apparatus comprising:
- a rack for supporting at least one flowpath assembly cartridge; and
- at least one media flowpath assembly cartridge, said cartridge including:
  - a housing;
  - a control interface;
  - a non-invasive sensor; and
  - a sterile media perfusion flowpath loop removable from said housing without breaching flowpath sterility, said media perfusion loop comprising:
    - a pump;
    - at least one valve adapted to prevent or divert media flow;
    - at least one biochamber in fluid communication with the pump and the at least one valve;
    - a gas permeable membrane in fluid communication with the pump and the at least one valve;
    - a media reservoir in fluid communication with the pump and the at least one valve; and
    - a flow sensor removably positionable within the non-invasive sensor.

3. A media flowpath assembly cartridge, comprising:
- a housing;
- a control interface;
- a sterile media perfusion flowpath loop removable from said housing without breaching flowpath sterility, said media perfusion loop comprising:
  - a pump;
  - at least one valve adapted to prevent or divert media flow;
  - at least one biochamber in fluid communication with the pump and the at least one valve;
  - a gas permeable membrane in fluid communication with the pump and the at least one valve; and
  - a media reservoir in fluid communication with the pump and the at least one valve;
- wherein said at least one biochamber is convertible for use in static cell culture or in a cell perfusion apparatus and comprises:
  - a vessel;
  - a cover removably connectable to the vessel;
  - a gasket comprising one or more sealing interfaces between the vessel and the cover; and
  - at least one insert positioned between the vessel and the cover, thereby partitioning the space between the vessel and the cover into a first chamber and a second chamber;
- wherein the gasket comprises two or more sealing interfaces between the vessel and the cover.

4. The cartridge of claim 3, wherein said biochamber further comprises at least one air gap between said two or more sealing interfaces.

5. The cartridge of claim 3, wherein said two or more sealing interfaces are capable of indicating seating of said interfaces by a color change.

* * * * *